(12) United States Patent
Jung et al.

(10) Patent No.: US 10,188,703 B2
(45) Date of Patent: Jan. 29, 2019

(54) METHOD FOR TREATING DIABETES MELLITUS BY A COMPOSITION COMPRISING INSULIN AND A GLP-1/GLUCAGON DUAL AGONIST

(71) Applicant: HANMI PHARM. CO., LTD., Hwaseong-si, Gyeonggi-do (KR)

(72) Inventors: Sung Youb Jung, Yongin-si (KR); Sang Youn Hwang, Hwaseong-si (KR); Seung Su Kim, Seoul (KR); In Young Choi, Yongin-si (KR); Se Chang Kwon, Seoul (KR)

(73) Assignee: HANMI PHARM. CO., LTD., Suwon-si (KR)

( * ) Notice: Subject to any disclaimer, the term of this patent is extended or adjusted under 35 U.S.C. 154(b) by 0 days.

(21) Appl. No.: 15/315,020

(22) PCT Filed: Jun. 1, 2015

(86) PCT No.: PCT/KR2015/005455
§ 371 (c)(1),
(2) Date: Nov. 30, 2016

(87) PCT Pub. No.: WO2015/183054
PCT Pub. Date: Dec. 3, 2015

(65) Prior Publication Data
US 2017/0196943 A1 Jul. 13, 2017

(30) Foreign Application Priority Data
May 30, 2014 (KR) ........................ 10-2014-0066554

(51) Int. Cl.
| | |
|---|---|
| *A61K 38/28* | (2006.01) |
| *A61K 38/26* | (2006.01) |
| *C07K 16/46* | (2006.01) |
| *C07K 19/00* | (2006.01) |
| *A61K 47/68* | (2017.01) |
| *A61K 47/60* | (2017.01) |
| *A61K 47/50* | (2017.01) |

(52) U.S. Cl.
CPC .............. *A61K 38/28* (2013.01); *A61K 38/26* (2013.01); *A61K 47/50* (2017.08); *A61K 47/60* (2017.08); *A61K 47/68* (2017.08); *A61K 47/6811* (2017.08); *A61K 47/6889* (2017.08); *C07K 16/46* (2013.01); *C07K 19/00* (2013.01); *C07K 2317/52* (2013.01); *C07K 2317/53* (2013.01); *C07K 2319/00* (2013.01); *C07K 2319/30* (2013.01)

(58) Field of Classification Search
CPC ................................ A61K 38/26; A61K 38/28
See application file for complete search history.

(56) References Cited

U.S. PATENT DOCUMENTS

| | | | |
|---|---|---|---|
| 5,175,145 A | 12/1992 | Cooper | |
| 5,422,339 A | 6/1995 | Eisenbarth et al. | |
| 5,424,286 A | 6/1995 | Eng | |
| 6,403,764 B1 | 6/2002 | Dubaquie et al. | |
| 7,736,653 B2 | 6/2010 | Kim et al. | |
| 7,790,677 B2 | 9/2010 | Zimmerman et al. | |
| 8,476,230 B2 | 6/2013 | Song et al. | |
| 9,165,768 B2 | 10/2015 | Kang | |
| 9,341,445 B2 | 5/2016 | de Haas et al. | |
| 9,422,349 B2 | 8/2016 | Jung et al. | |
| 9,526,764 B2 | 12/2016 | Werner et al. | |
| 9,528,180 B2 | 12/2016 | Becker et al. | |
| 9,669,073 B2 | 6/2017 | Kim et al. | |
| 2005/0288248 A1 | 12/2005 | Pan et al. | |
| 2006/0241019 A1 | 10/2006 | Bridon et al. | |
| 2010/0105877 A1 | 4/2010 | Song et al. | |
| 2010/0216692 A1 | 8/2010 | Brunner-Schwarz et al. | |
| 2011/0077197 A1 | 3/2011 | Habermann et al. | |
| 2011/0152185 A1 | 6/2011 | Plum et al. | |
| 2011/0257091 A1 | 10/2011 | DiMarchi et al. | |
| 2012/0021978 A1 | 1/2012 | Werner et al. | |
| 2012/0071402 A1* | 3/2012 | Madsen | A61K 38/28 514/5.3 |
| 2012/0100141 A1 | 4/2012 | Herring et al. | |
| 2012/0184488 A1 | 7/2012 | Weiss | |
| 2013/0028918 A1 | 1/2013 | Song et al. | |
| 2013/0122023 A1 | 5/2013 | Woo et al. | |
| 2014/0120120 A1 | 5/2014 | Woo et al. | |
| 2014/0212440 A1* | 7/2014 | Jung | C07K 14/575 424/178.1 |
| 2015/0190528 A1 | 7/2015 | Lim et al. | |
| 2016/0008483 A1 | 1/2016 | Hwang et al. | |
| 2017/0143802 A1 | 5/2017 | Kim et al. | |

FOREIGN PATENT DOCUMENTS

| | | |
|---|---|---|
| CL | 1235-2003 | 4/2004 |
| CL | 00018-2009 | 6/2009 |

(Continued)

OTHER PUBLICATIONS

Betts et al., "Amino Acid Properties and Consequences of Substitutions," Bioinformatics for Geneticists, Chapter 14, John Wiley & Sons, Ltd., 2003, pp. 289-316.

(Continued)

*Primary Examiner* — Gyan Chandra
(74) *Attorney, Agent, or Firm* — Sughrue Mion, PLLC

(57) ABSTRACT

A composition for preventing or treating diabetes mellitus includes insulin and a GLP-1/glucagon dual agonist. The composition can inhibit the weight gain and reduce the danger of hypoglycemia due to the administration of insulin, lower the administration dose and greatly improve the compliance of drugs through a combined administration of a long-acting insulin conjugate and a long-acting GLP-1/glucagon dual agonist conjugate. In addition, the long-acting insulin conjugate and the long-acting GLP-1/glucagon dual agonist conjugate can improve the in vivo sustainability and stability because an insulin and a GLP-1/glucagon dual agonist are linked to the immunoglobulin Fc region via a non-peptidyl linker. A method for preventing or treat diabetes mellitus includes administration of the insulin and a GLP-1/glucagon dual agonist.

15 Claims, 2 Drawing Sheets

Specification includes a Sequence Listing.

(56) References Cited

FOREIGN PATENT DOCUMENTS

| | | |
|---|---|---|
| CL | 201603075 | 11/2016 |
| DE | 102 27 232 A1 | 1/2004 |
| DE | 10 2008 003 568 A1 | 7/2009 |
| DE | 10 2008 025 008 A1 | 11/2009 |
| EP | 2017288 A1 | 1/2009 |
| EP | 2700654 A1 | 2/2014 |
| EP | 2963056 A1 | 1/2016 |
| JP | 2012-62311 A | 3/2012 |
| JP | 2012-229214 A | 11/2012 |
| KR | 10-2005-0121748 A | 12/2005 |
| KR | 10-0725315 B1 | 6/2007 |
| KR | 10-2010-0111683 A | 10/2010 |
| KR | 10-2011-0084956 A | 7/2011 |
| KR | 10-2011-0092253 A | 8/2011 |
| KR | 10-1058209 B1 | 8/2011 |
| KR | 10-1058290 B1 | 8/2011 |
| KR | 10-2011-0111267 A | 10/2011 |
| KR | 10-2011-0134209 A | 12/2011 |
| KR | 10-2011-0134210 A | 12/2011 |
| KR | 10-2011-0137819 A | 12/2011 |
| KR | 10-2012-0135123 A | 12/2012 |
| KR | 10-2012-0137271 A | 12/2012 |
| KR | 10-2012-0139579 A | 12/2012 |
| KR | 10-1231431 B1 | 2/2013 |
| KR | 10-1324828 B1 | 11/2013 |
| KR | 10-1330868 B1 | 11/2013 |
| KR | 10-2014-0006938 A | 1/2014 |
| KR | 10-2014-0022909 A | 2/2014 |
| KR | 10-2014-0106452 A | 9/2014 |
| TW | 201204382 A1 | 2/2012 |
| WO | 96/32478 A1 | 10/1996 |
| WO | 97/34631 A1 | 9/1997 |
| WO | 2009/129250 A2 | 10/2009 |
| WO | 2010/080606 A1 | 7/2010 |
| WO | 2010/080609 A1 | 7/2010 |
| WO | 2011/028813 A2 | 3/2011 |
| WO | 2011/122921 A2 | 10/2011 |
| WO | 2012/015692 A2 | 2/2012 |
| WO | 2012/098462 A1 | 7/2012 |
| WO | 2012/165915 A2 | 12/2012 |
| WO | 2012/167251 A1 | 12/2012 |
| WO | 2012/169798 A2 | 12/2012 |
| WO | 2012/173422 A1 | 12/2012 |
| WO | 2013/110069 A1 | 7/2013 |
| WO | 2013/133667 A1 | 9/2013 |
| WO | 2014/017843 A1 | 1/2014 |
| WO | 2014/017845 A2 | 1/2014 |
| WO | 2014/017847 A1 | 1/2014 |
| WO | 2014/017849 A1 | 1/2014 |
| WO | 2014/049610 A2 | 4/2014 |
| WO | 2014/073842 A1 | 5/2014 |
| WO | 2014/133324 A1 | 9/2014 |
| WO | 2015/183038 A1 | 12/2015 |

OTHER PUBLICATIONS

NCBI, Genbank AAA72172.1, (Apr. 27, 1993)/ "Synthetic Preproinsulin [synthetic construct] NCBI," located at https://www.ncbi.nlm.nih.gov/protein/AAA72172.1?report=gpwithparts&log$=seqview, last visited Jun. 20, 2017.
European Patent Office, Communication dated Sep. 20, 2017 by the European Patent Office in counterpart European Patent Application No. EP 15 73 7856.3.
Fosgerau et al., "Combination of Long-Acting Insulin with the Dual GluGLP-1 Agonist ZP2929 Causes Improved Glycemic Control without Body Weight Gain in db/db Mice", 1527-P, Diabetes (Suppl 1), vol. 60, 2011, p. A418, XP-002775063.
European Patent Office; Communication dated Nov. 17, 2017 in counterpart application No. 15799077.1.
Ngo J.T., Marks J, Karplus M., "Computational Complexity, Protein Structure Prediction, and the Levinthal Paradox," The Protein Folding Problem and Teritary Structure Prediction, K. Merc Jr. and S. Le Grand Edition, 1994, pp. 491-495.
UniProtKB A6XGL2, pp. 1-5. Integrated in UniProtKB/TrEMBL Aug. 21, 2007.
Yampolsky et al., "The Exchangeability of Amino Acids in Proteins," Genetics, 170: 1459-1472, 2005.
Rudinger J., "Characteristics of the Amino Acids as Components of a Peptide Hormone Sequence," Peptide Hormones, J.A. Parsons Edition, University Park Press, Jun. 1976, pp. 1-7. (8 pages total).
"Designing Custom Peptides," from SIGMA Genosys, pp. 1-2. Accessed Dec. 16, 2004.
Schinzel R., Drueckes P., "The Phosphate Recognition Site of *Escherichia Coli* Maltodextrin Phosphorylase," FEBS, Jul. 1991. 286(1,2): 125-128.
Berendsen HJC, "A Glimpse of the Holy Grail?" Science, 1998, 282: 642-643.
Voet D, Voet JG, Biochemistry, Second Edition, John Wiley & Sons, Inc., 1995, pp. 235-241. (9 pages).
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.
Betts et al., "Amino Acid Properties and Consequences of Substitutions," Bioinformatices for Geneticists, Chapter 14, John Wiley & Sons, Ltd, 2003, pp. 289-316.
Jørgensen, A. et al (Apr. 1996). "Solution Structure of the Superactive Monomeric Des-[Phe (B25)] Human Insulin Mutant: Elucidation of the Strucutral Basis for the Monomerization of Des-[Phe (B25)] Insulin and the Dimerization of Native Insulin," 257(3):684-699.
Keller, D. et al. (2001). "Flexibility and Bioactivity of Insulin: an NMR Investigation of the Solution and Folding of an Unusually Flexible Human Insulin Mutant with Increased Biological Activity," Biochemistry 40(35):10732-10740.
NCBI, Genbank AAA72172.1, (Apr. 27, 1993)/ "Synthetic Preproinsulin [synthetic contruct] NCBI," located at https://www.ncbi.nlm.nih.gov/protein/AAA72172.1?report=gpwithparts&log$=seqview, last visited on Jun. 20, 2017.
NCBI, Genbank AKI70564.1 (Jun. 1, 2015). "INS, Partial [synthetic construct]" located at <https://www.ncbi.nlm.nih.gov/protein/AKI70564.1?report=gpwithparts&log$=seqview> last visited on Jun. 20, 2017.
NCBI, Genbank NM_001291897.1, (May 13, 2015). "*Homo Sapiens* Insulin (INS), Transcript Variant 4, mRNA," located at <https://www.ncbi.nlm.nih.gov/nuccore/NM-001291897.1?report=gpwithparts&log$=seqview&sat=4&satkey=139944924>, Last visited on Jun. 20, 2017, 4 pages.
Uhlman, E. et al. (Jun. 1990). "Antisense Oligonucleotides: A New Therapeutic Principle," Chemical Reviews 90(4):543-584.
Chilean Patent Office, Communication dated Jul. 13, 2017 by the Chilean Patent Office in counterpart Chilean Patent Application No. 201601844.
European Patent Office, Communication dated Sep. 20, 2017 by the European Patent Office in counterpart European Patent Application No. EP 15 73 7856.
Authier F. et al. (1998) "Uptake and Metabolic Fate of [$His^{48}$, $His^{b4}$, $Glu^{B10}$, $His^{B27}$] Insulin in Rat Liver In Vivo," Biochem J. 332;421-30.
Duckworth, W.C. et al. (Oct. 1998). "Insulin Degredation: Process and Potential," Endocr Rev. 19(5):608-24.
Senshang Lin, et al., "Comparative Pharmacokinetic and Pharmacodynamic Studies of Human Insulin and Analogues in Chronic Diabetic Yucatan Minipigs", The Journal of Pharmacology and Experimental Therapeutics, Apr. 13, 1998, pp. 959-966, vol. 286, No. 2.
Ribel et al., "Equivalent In Vivo Biological Activity of Insulin Analogues and Human Insulin Despite Different In Vitro Potencies," Diabetes, vol. 39, Sep. 1990, pp. 1033-1039. (7 pages total).
Valera, M. M. et al. (Dec. 2003). "Insulin Clearance in Obesity," J Am Coll Ntur. 22(6):487-93, Abstract Only.
United States Patent and Trademark Office communication dated Jan. 17, 2017 in counterpart U.S. Appl. No. 14/769,495.
European Patent Office; Communication dated May 10, 2017, in counterpart European application No. 14757629.2.

(56) References Cited

OTHER PUBLICATIONS

United States Patent and Trademark Office communication dated Jul. 19, 2017 in counterpart U.S. Appl. No. 14/769,495.
Chen et al., "Four New Monomeric Insulins Obtained by Alanine Scanning the Dimer-Forming Surface of the Insulin Molecule," Protein Eng'g 13:779-782 (2000).
Nakagawa et al., "Chiral Mutagenesis of Insulin, Contribution of the B20-B23 β-turn to Activity and Stability," J. Biol. Chem. 281:22386-22396, (2006).
Chu et al., "The A14 Position of Insulin Tolerates Considerable Structural Alterations with Modest Effects on the Biological Behavior of the Hormone", Journal of Protein Chemistry, vol. 11, No. 5, 1992, pp. 571-577.
Mohan. "Which Insulin to Use? Human or Animal?," Curr. Sci, 83:1544-1547 (2002).
European Patent Office; Communication dated Nov. 30, 2016, in counterpart European Application No. 14757629.2.
Colombian Patent Office; Communication dated Nov. 8, 2016, in counterpart Colombian application No. 15227010.
Kristensen et al., "Alanine Scanning Mutagenesis of Insulin," The Journal of Biological Chemistry, vol. 272, No. 20, 1997, pp. 12978-12983. (7 pages total).
Chile Patent Office; Communication dated Aug. 22, 2016, issued in corresponding Application No. 2015-002330.
R. Vigneri, et al., "Insulin and its analogs: actions via insulin and IGF receptors", Acta Diabetol, 2010, pp. 271-278, vol. 47, No. 4.
NCBI, "insulin preproprotein [*Homo sapiens*]", NCBI Reference Sequence: NP_000198.1, Feb. 17, 2013, [online]<http:// www.ncbi.nlm.nih.gov/protein/4557671?sat=17&satkey=22757282> retrieved on Mar. 31, 2014.
Brange et al., "Monomeric Insulins and Their Experimental and Clinical Implications," Diabetes Care, vol. 13, No. 9, Sep. 1990, pp. 923-954. (32 pages total).
International Searching Authority, International Search Report for PCT/KR2014/001593 dated May 22, 2014.
International Searching Authority, Written Opinion of the International Search Authority for PCT/KR2014/001593 dated May 22, 2014.
Taiwanese Intellectual Property Office; Communication dated Sep. 11, 2017 in counterpart application No. 103106674.
United States Patent and Trademark Office; Communication dated Sep. 14, 2017 in counterpart U.S. Appl. No. 15/250,459.
United States Patent and Trademark Office; Communication dated Sep. 8, 2017 in counterpart U.S. Appl. No. 15/313,501.
Intellectual Property Office of Singapore, Communication dated Oct. 3, 2017 in counterpart application No. 11201609564T.
European Patent Office, Communication dated Nov. 10, 2017 in counterpart application No. 15799334.6.
Martin Lorenz et al., "Recent progress and future options in the development of GLP-1 receptor agonists for the treatment of diabesity", Bioorganic & Medicinal Chemistry Letters, 2013, pp. 4011-4018, vol. 23, No. 14.
International Searching Authority, International Search Report of PCT/KR2015/005455 dated Aug. 24, 2015 [PCT/ISA/210].
International Searching Authority, Written Opinion of PCT/KR2015/005455 dated Aug. 24, 2015 [PCT/ISA/237].
United States Patent and Trademark Office; Notice of Allowance dated Feb. 26, 2018 in U.S. Appl. No. 15/250,459.
United States Patent and Trademark Office; Non-Final Rejection dated Jan. 16, 2018 in U.S. Appl. No. 15/113,027.
United States Patent and Trademark Office; Final Rejection dated Mar. 8, 2018 in U.S. Appl. No. 15/313,501.
United States Patent and Trademark Office; Non-Final Rejection dated Apr. 5, 2018 in U.S. Appl. No. 14/769,495.
Intellectual Property Office of Singapore; Communication dated Jan. 26, 2018 in counterpart Singaporean application No. 11201609872Y.
Colombian Patent and Trademark Office; communication dated Feb. 16, 2018, in Colombian application No. NC2016/0004794.
Chinese Patent and Trademark Office; communication dated Mar. 1, 2018, in Chinese Patent Application No. 201480006998.4.
Japanese Patent Office; Communication dated Jan. 16, 2018 in counterpart Japanese application No. 2015-559199.
Saudi Arabian Patent Office; Communication dated Apr. 30, 2016 in counterpart Saudi Arabian application No. 5153609363.
Colombian Patent Office; Communication dated Aug. 24, 2017 in counterpart Colombian application No. 15227010.
Chilean Patent Office; Communication dated May 29, 2018 issued in counterpart Chilean Application No. 201603069.
United States Patent and Trademark Office; Final Rejection dated Jul. 17, 2018 in co-pending U.S. Appl. No. 15/113,027.

\* cited by examiner

[Fig. 1]
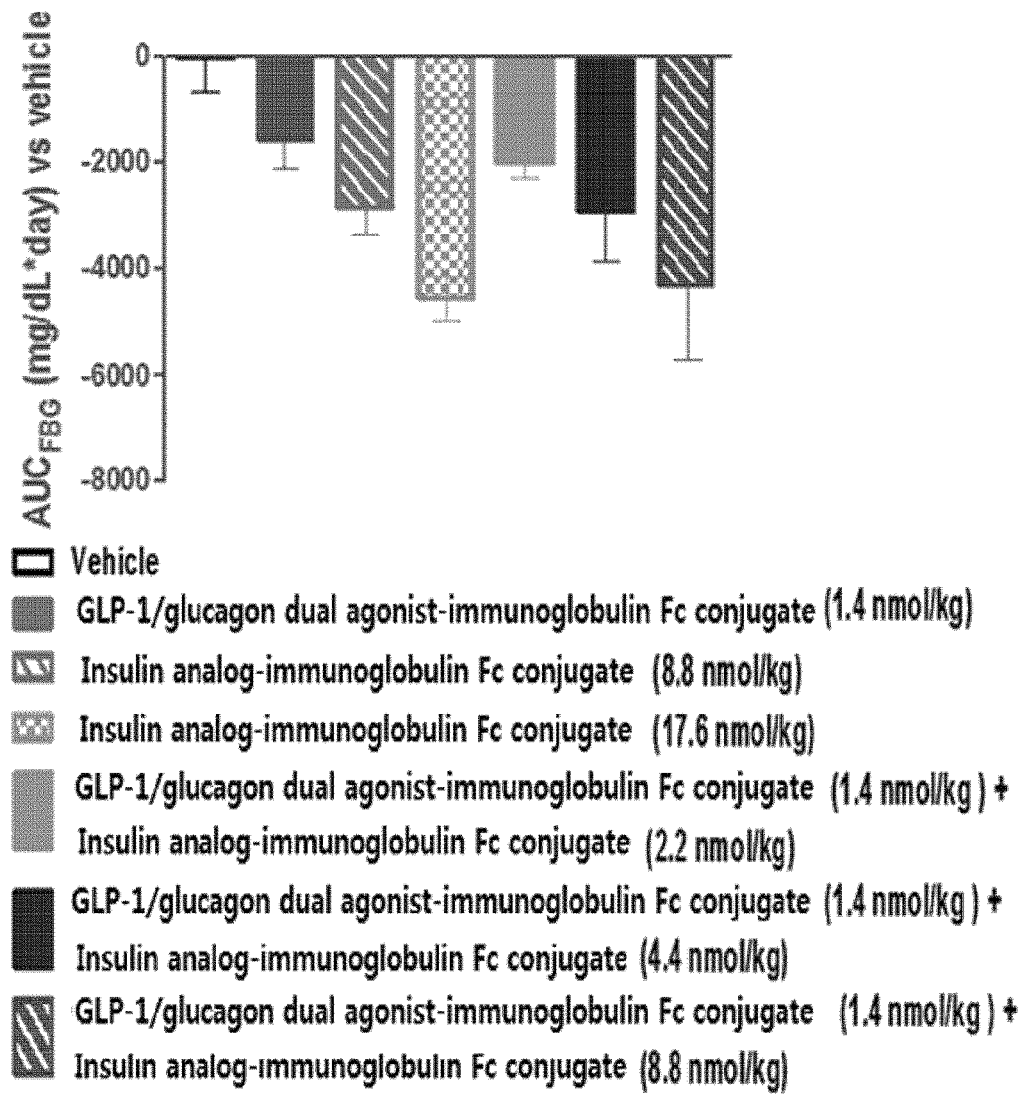

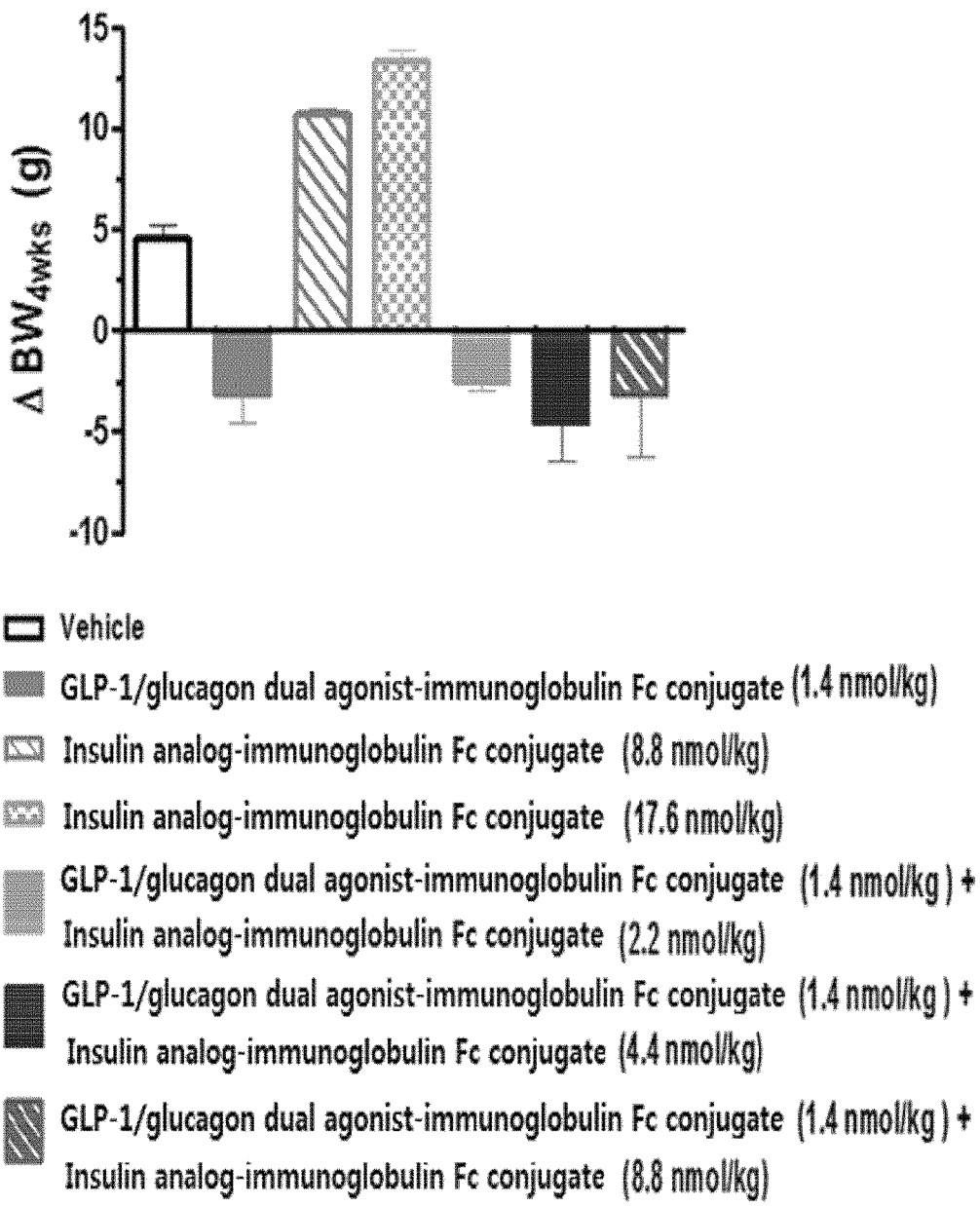

SEQUENCE LISTING

<160> NUMBER OF SEQ ID NOS: 72

<210> SEQ ID NO 1
<211> LENGTH: 39
<212> TYPE: DNA
<213> ORGANISM: Artificial Sequence
<220> FEATURE:
<223> OTHER INFORMATION: Primer

<400> SEQUENCE: 1
gggtccctgc agaagcgtgc gattgtggaa caatgctgt                                 39

<210> SEQ ID NO 2
<211> LENGTH: 39
<212> TYPE: DNA
<213> ORGANISM: Artificial Sequence
<220> FEATURE:
<223> OTHER INFORMATION: Primer

<400> SEQUENCE: 2
acagcattgt tccacaatcg cacgcttctg cagggaccc                                 39

<210> SEQ ID NO 3
<211> LENGTH: 39
<212> TYPE: DNA
<213> ORGANISM: Artificial Sequence
<220> FEATURE:
<223> OTHER INFORMATION: Primer

<400> SEQUENCE: 3
tccctgcaga agcgtggcgc ggtggaacaa tgctgtacc                                 39

<210> SEQ ID NO 4
<211> LENGTH: 39
<212> TYPE: DNA
<213> ORGANISM: Artificial Sequence
<220> FEATURE:
<223> OTHER INFORMATION: Primer

<400> SEQUENCE: 4
ggtacagcat tgttccaccg cgccacgctt ctgcaggga                                 39

<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5
ctctaccagc tggaaaacgc gtgtaactga ggatcc                                    36

<210> SEQ ID NO 6
<211> LENGTH: 36
<212> TYPE: DNA
<213> ORGANISM: Artificial Sequence
<220> FEATURE:
<223> OTHER INFORMATION: Primer

<400> SEQUENCE: 6
ggatcctcag ttacacgcgt tttccagctg gtagag                                    36

<210> SEQ ID NO 7
<211> LENGTH: 39
<212> TYPE: DNA
<213> ORGANISM: Artificial Sequence

```
<220> FEATURE:
<223> OTHER INFORMATION: Primer

<400> SEQUENCE: 7
gttaaccaac acttgtgtgc gtcacacctg gtggaagct                              39

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
agcttccacc aggtgtgacg cacacaagtg ttggttaac                              39

<210> SEQ ID NO 9
<211> LENGTH: 39
<212> TYPE: DNA
<213> ORGANISM: Artificial Sequence
<220> FEATURE:
<223> OTHER INFORMATION: Primer

<400> SEQUENCE: 9
ctagtgtgcg gggaacgagc gttcttctac acacccaag                              39

<210> SEQ ID NO 10
<211> LENGTH: 39
<212> TYPE: DNA
<213> ORGANISM: Artificial Sequence
<220> FEATURE:
<223> OTHER INFORMATION: Primer

<400> SEQUENCE: 10
cttgggtgtg tagaagaacg ctcgttcccc gcacactag                              39

<210> SEQ ID NO 11
<211> LENGTH: 39
<212> TYPE: DNA
<213> ORGANISM: Artificial Sequence
<220> FEATURE:
<223> OTHER INFORMATION: Primer

<400> SEQUENCE: 11
gtgtgcgggg aacgaggcgc gttctacaca cccaagacc                              39

<210> SEQ ID NO 12
<211> LENGTH: 39
<212> TYPE: DNA
<213> ORGANISM: Artificial Sequence
<220> FEATURE:
<223> OTHER INFORMATION: Primer

<400> SEQUENCE: 12
ggtcttgggt gtgtagaacg cgcctcgttc cccgcacac                              39

<210> SEQ ID NO 13
<211> LENGTH: 39
<212> TYPE: DNA
<213> ORGANISM: Artificial Sequence
<220> FEATURE:
<223> OTHER INFORMATION: Primer

<400> SEQUENCE: 13
tgcggggaac gaggcttcgc gtacacaccc aagacccgc                              39
```

```
<210> SEQ ID NO 14
<211> LENGTH: 39
<212> TYPE: DNA
<213> ORGANISM: Artificial Sequence
<220> FEATURE:
<223> OTHER INFORMATION: Primer

<400> SEQUENCE: 14
gcgggtcttg ggtgtgtacg cgaagcctcg ttccccgca                      39

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
ccagcatctg ctccctcgaa cagctggaga actactg                         37

<210> SEQ ID NO 16
<211> LENGTH: 37
<212> TYPE: DNA
<213> ORGANISM: Artificial Sequence
<220> FEATURE:
<223> OTHER INFORMATION: Primer

<400> SEQUENCE: 16
cagtagttct ccagctgttc gagggagcag atgctgg                         37

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17
cagcatctgc tccctcaacc agctggagaa ctac                            34

<210> SEQ ID NO 18
<211> LENGTH: 34
<212> TYPE: DNA
<213> ORGANISM: Artificial Sequence
<220> FEATURE:
<223> OTHER INFORMATION: Primer

<400> SEQUENCE: 18
gtagttctcc agctggttga gggagcagat gctg                            34

<210> SEQ ID NO 19
<211> LENGTH: 258
<212> TYPE: DNA
<213> ORGANISM: Artificial Sequence
<220> FEATURE:
<223> OTHER INFORMATION: Analog 1

<400> SEQUENCE: 19
ttcgttaacc aacacttgtg tggctcacac ctggtggaag ctctctacct agtgtgcggg    60
gaacgaggct tcttctacac acccaagacc cgccgggagg cagaggacct gcaggtgggg   120
caggtggagc tgggcggggg ccctggtgca ggcagcctgc agcccttggc cctggagggg   180
tccctgcaga agcgtgcgat tgtgaacaa tgctgtacca gcatctgctc cctctaccag    240
ctggagaact actgcaac                                                258
```

<210> SEQ ID NO 20
<211> LENGTH: 86
<212> TYPE: PRT
<213> ORGANISM: Artificial Sequence
<220> FEATURE:
<223> OTHER INFORMATION: Analog 1

<400> SEQUENCE: 20

```
Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Arg Arg
             20                  25                  30

Glu Ala Glu Asp Leu Gln Val Gly Gln Val Glu Leu Gly Gly Gly Pro
         35                  40                  45

Gly Ala Gly Ser Leu Gln Pro Leu Ala Leu Glu Gly Ser Leu Gln Lys
     50                  55                  60

Arg Ala Ile Val Glu Gln Cys Cys Thr Ser Ile Cys Ser Leu Tyr Gln
 65                  70                  75                  80

Leu Glu Asn Tyr Cys Asn
                 85
```

<210> SEQ ID NO 21
<211> LENGTH: 258
<212> TYPE: DNA
<213> ORGANISM: Artificial Sequence
<220> FEATURE:
<223> OTHER INFORMATION: Analog 2

<400> SEQUENCE: 21

```
ttcgttaacc aacacttgtg tggctcacac ctggtggaag ctctctacct agtgtgcggg      60
gaacgaggct tcttctacac acccaagacc cgccggagg cagaggacct gcaggtgggg      120
caggtggagc tgggcggggg ccctggtgca ggcagcctgc agcccttggc cctggagggg     180
tccctgcaga gcgtggcgc ggtggaacaa tgctgtacca gcatctgctc cctctaccag     240
ctggagaact actgcaac                                                   258
```

<210> SEQ ID NO 22
<211> LENGTH: 86
<212> TYPE: PRT
<213> ORGANISM: Artificial Sequence
<220> FEATURE:
<223> OTHER INFORMATION: Analog 2

<400> SEQUENCE: 22

```
Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Arg Arg
             20                  25                  30

Glu Ala Glu Asp Leu Gln Val Gly Gln Val Glu Leu Gly Gly Gly Pro
         35                  40                  45

Gly Ala Gly Ser Leu Gln Pro Leu Ala Leu Glu Gly Ser Leu Gln Lys
     50                  55                  60

Arg Gly Ala Val Glu Gln Cys Cys Thr Ser Ile Cys Ser Leu Tyr Gln
 65                  70                  75                  80

Leu Glu Asn Tyr Cys Asn
                 85
```

<210> SEQ ID NO 23
<211> LENGTH: 258
<212> TYPE: DNA
<213> ORGANISM: Artificial Sequence
<220> FEATURE:
<223> OTHER INFORMATION: Analog 3

<400> SEQUENCE: 23

```
ttcgttaacc aacacttgtg tggctcacac ctggtggaag ctctctacct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctctaccag     240
ctggagaacg cgtgcaac                                                   258
```

<210> SEQ ID NO 24
<211> LENGTH: 86
<212> TYPE: PRT
<213> ORGANISM: Artificial Sequence
<220> FEATURE:
<223> OTHER INFORMATION: Analog 3

<400> SEQUENCE: 24

```
Phe Val Asn Gln His Leu Cys Gly Ser His Leu Val Glu Ala Leu Tyr
  1               5                  10                  15

Leu Val Cys Gly Glu Arg Gly Phe Phe Tyr Thr Pro Lys Thr Arg Arg
             20                  25                  30

Glu Ala Glu Asp Leu Gln Val Gly Gln Val Leu Gly Gly Gly Pro
         35                  40                  45

Gly Ala Gly Ser Leu Gln Pro Leu Ala Leu Glu Gly Ser Leu Gln Lys
     50                  55                  60

Arg Gly Ile Val Glu Gln Cys Cys Thr Ser Ile Cys Ser Leu Tyr Gln
 65                  70                  75                  80

Leu Glu Asn Ala Cys Asn
                 85
```

<210> SEQ ID NO 25
<211> LENGTH: 258
<212> TYPE: DNA
<213> ORGANISM: Artificial Sequence
<220> FEATURE:
<223> OTHER INFORMATION: Analog 4

<400> SEQUENCE: 25

```
ttcgttaacc aacacttgtg tgcgtcacac ctggtggaag ctctctacct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctctaccag     240
ctggagaact actgcaac                                                   258
```

<210> SEQ ID NO 26
<211> LENGTH: 86
<212> TYPE: PRT
<213> ORGANISM: Artificial Sequence
<220> FEATURE:
<223> OTHER INFORMATION: Analog 4

```
<400> SEQUENCE: 26

Phe Val Asn Gln His Leu Cys Ala Ser His Leu Val Glu Ala Leu Tyr
  1               5                  10                  15

Leu Val Cys Gly Glu Arg Gly Phe Phe Tyr Thr Pro Lys Thr Arg Arg
             20                  25                  30

Glu Ala Glu Asp Leu Gln Val Gly Gln Val Glu Leu Gly Gly Gly Pro
         35                  40                  45

Gly Ala Gly Ser Leu Gln Pro Leu Ala Leu Glu Gly Ser Leu Gln Lys
     50                  55                  60

Arg Gly Ile Val Glu Gln Cys Cys Thr Ser Ile Cys Ser Leu Tyr Gln
 65                  70                  75                  80

Leu Glu Asn Tyr Cys Asn
                 85

<210> SEQ ID NO 27
<211> LENGTH: 258
<212> TYPE: DNA
<213> ORGANISM: Artificial Sequence
<220> FEATURE:
<223> OTHER INFORMATION: Analog 5

<400> SEQUENCE: 27
ttcgttaacc aacacttgtg tggctcacac ctggtggaag ctctctacct agtgtgcggg     60
gaacgagcgt tcttctacac acccaagacc cgccgggagg cagaggacct gcaggtgggg    120
caggtggagc tgggcggggg ccctggtgca ggcagcctgc agcccttggc cctggagggg    180
tccctgcaga agcgtggcat tgtggaacaa tgctgtacca gcatctgctc cctctaccag    240
ctggagaact actgcaac                                                  258

<210> SEQ ID NO 28
<211> LENGTH: 86
<212> TYPE: PRT
<213> ORGANISM: Artificial Sequence
<220> FEATURE:
<223> OTHER INFORMATION: Analog 5

<400> SEQUENCE: 28

Phe Val Asn Gln His Leu Cys Gly Ser His Leu Val Glu Ala Leu Tyr
  1               5                  10                  15

Leu Val Cys Gly Glu Arg Ala Phe Phe Tyr Thr Pro Lys Thr Arg Arg
             20                  25                  30

Glu Ala Glu Asp Leu Gln Val Gly Gln Val Glu Leu Gly Gly Gly Pro
         35                  40                  45

Gly Ala Gly Ser Leu Gln Pro Leu Ala Leu Glu Gly Ser Leu Gln Lys
     50                  55                  60

Arg Gly Ile Val Glu Gln Cys Cys Thr Ser Ile Cys Ser Leu Tyr Gln
 65                  70                  75                  80

Leu Glu Asn Tyr Cys Asn
                 85

<210> SEQ ID NO 29
<211> LENGTH: 258
<212> TYPE: DNA
<213> ORGANISM: Artificial Sequence
<220> FEATURE:
<223> OTHER INFORMATION: Analog 6
```

```
<400> SEQUENCE: 29
ttcgttaacc aacacttgtg tggctcacac ctggtggaag ctctctacct agtgtgcggg    60
gaacgaggcg cgttctacac acccaagacc cgccgggagg cagaggacct gcaggtgggg   120
caggtggagc tgggcggggg ccctggtgca ggcagcctgc agcccttggc cctggagggg   180
tccctgcaga agcgtggcat tgtggaacaa tgctgtacca gcatctgctc cctctaccag   240
ctggagaact actgcaac                                                 258

<210> SEQ ID NO 30
<211> LENGTH: 86
<212> TYPE: PRT
<213> ORGANISM: Artificial Sequence
<220> FEATURE:
<223> OTHER INFORMATION: Analog 6

<400> SEQUENCE: 30

Phe Val Asn Gln His Leu Cys Gly Ser His Leu Val Glu Ala Leu Tyr
  1               5                  10                  15

Leu Val Cys Gly Glu Arg Gly Ala Phe Tyr Thr Pro Lys Thr Arg Arg
                 20                  25                  30

Glu Ala Glu Asp Leu Gln Val Gly Gln Val Glu Leu Gly Gly Gly Pro
             35                  40                  45

Gly Ala Gly Ser Leu Gln Pro Leu Ala Leu Glu Gly Ser Leu Gln Lys
         50                  55                  60

Arg Gly Ile Val Glu Gln Cys Cys Thr Ser Ile Cys Ser Leu Tyr Gln
 65                  70                  75                  80

Leu Glu Asn Tyr Cys Asn
                 85

<210> SEQ ID NO 31
<211> LENGTH: 258
<212> TYPE: DNA
<213> ORGANISM: Artificial Sequence
<220> FEATURE:
<223> OTHER INFORMATION: Analog 7

<400> SEQUENCE: 31
ttcgttaacc aacacttgtg tggctcacac ctggtggaag ctctctacct agtgtgcggg    60
gaacgaggct cgcgtacac acccaagacc cgccgggagg cagaggacct gcaggtgggg   120
caggtggagc tgggcggggg ccctggtgca ggcagcctgc agcccttggc cctggagggg   180
tccctgcaga agcgtggcat tgtggaacaa tgctgtacca gcatctgctc cctctaccag   240
ctggagaact actgcaac                                                 258

<210> SEQ ID NO 32
<211> LENGTH: 86
<212> TYPE: PRT
<213> ORGANISM: Artificial Sequence
<220> FEATURE:
<223> OTHER INFORMATION: Analog 7

<400> SEQUENCE: 32

Phe Val Asn Gln His Leu Cys Gly Ser His Leu Val Glu Ala Leu Tyr
  1               5                  10                  15

Leu Val Cys Gly Glu Arg Gly Phe Ala Tyr Thr Pro Lys Thr Arg Arg
                 20                  25                  30

Glu Ala Glu Asp Leu Gln Val Gly Gln Val Glu Leu Gly Gly Gly Pro
             35                  40                  45
```

```
Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 33
<211> LENGTH: 261
<212> TYPE: DNA
<213> ORGANISM: Artificial Sequence
<220> FEATURE:
<223> OTHER INFORMATION: Analog 8

<400> SEQUENCE: 33
ttcgttaacc aacacttgtg tggctcacac ctggtggaag ctctctacct agtgtgcggg      60
gaacgaggct tcttctacac acccaagacc cgccggagg cagaggacct gcaggtgggg     120
caggtggagc tgggcggggg ccctggtgca ggcagcctgc agcccttggc cctggagggg    180
tccctgcaga agcgtggcat tgtggaacaa tgctgtacca gcatctgctc cctcgaacag    240
ctggagaact actgcaactg a                                              261

<210> SEQ ID NO 34
<211> LENGTH: 86
<212> TYPE: PRT
<213> ORGANISM: Artificial Sequence
<220> FEATURE:
<223> OTHER INFORMATION: Analog 8

<400> SEQUENCE: 34

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
                20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Glu Gln
65                  70                  75                  80

Leu Glu Asn Tyr Cys Asn
                85

<210> SEQ ID NO 35
<211> LENGTH: 261
<212> TYPE: DNA
<213> ORGANISM: Artificial Sequence
<220> FEATURE:
<223> OTHER INFORMATION: Analog 9

<400> SEQUENCE: 35
ttcgttaacc aacacttgtg tggctcacac ctggtggaag ctctctacct agtgtgcggg      60
gaacgaggct tcttctacac acccaagacc cgccggagg cagaggacct gcaggtgggg     120
caggtggagc tgggcggggg ccctggtgca ggcagcctgc agcccttggc cctggagggg    180
tccctgcaga agcgtggcat tgtggaacaa tgctgtacca gcatctgctc cctcaaccag    240
ctggagaact actgcaactg a                                              261
```

-continued

```
<210> SEQ ID NO 36
<211> LENGTH: 86
<212> TYPE: PRT
<213> ORGANISM: Artificial Sequence
<220> FEATURE:
<223> OTHER INFORMATION: Analog 9

<400> SEQUENCE: 36

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Asn Gln
65                  70                  75                  80

Leu Glu Asn Tyr Cys Asn
                85

<210> SEQ ID NO 37
<211> LENGTH: 21
<212> TYPE: PRT
<213> ORGANISM: Artificial Sequence
<220> FEATURE:
<223> OTHER INFORMATION: A chain of insulin

<400> SEQUENCE: 37

Gly Ile Val Glu Gln Cys Cys Thr Ser Ile Cys Ser Leu Tyr Gln Leu
 1               5                  10                  15

Glu Asn Tyr Cys Asn
            20

<210> SEQ ID NO 38
<211> LENGTH: 30
<212> TYPE: PRT
<213> ORGANISM: Artificial Sequence
<220> FEATURE:
<223> OTHER INFORMATION: B chain of insulin

<400> SEQUENCE: 38

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
            20                  25                  30

<210> SEQ ID NO 39
<211> LENGTH: 37
<212> TYPE: PRT
<213> ORGANISM: Homo sapiens
<220> FEATURE:
<223> OTHER INFORMATION: oxyntomodulin

<400> SEQUENCE: 39

His Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Lys Arg Asn
            20                  25                  30

Arg Asn Asn Ile Ala
        35
```

```
<210> SEQ ID NO 40
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (2)
<223> OTHER INFORMATION: Xaa = aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 40

His Xaa Gln Gly Thr Phe Thr Ser Asp Tyr Ser Lys Tyr Leu Asp Glu
 1               5                  10                  15

Lys Arg Ala Lys Glu Phe Val Gln Trp Leu Met Asn Thr Cys
            20                  25                  30

<210> SEQ ID NO 41
<211> LENGTH: 37
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.

<400> SEQUENCE: 41

Xaa Ser Gln Gly Thr Phe Thr Ser Asp Tyr Ser Lys Tyr Leu Asp Glu
 1               5                  10                  15

Glu Ala Val Arg Leu Phe Ile Glu Trp Leu Met Asn Thr Lys Arg Asn
            20                  25                  30

Arg Asn Asn Ile Ala
        35

<210> SEQ ID NO 42
<211> LENGTH: 39
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.

<400> SEQUENCE: 42

Xaa Ser Gln Gly Thr Phe Thr Ser Asp Tyr Ser Lys Tyr Leu Asp Glu
 1               5                  10                  15

Arg Arg Ala Gln Asp Phe Val Ala Trp Leu Lys Asn Thr Gly Pro Ser
            20                  25                  30

Ser Gly Ala Pro Pro Pro Ser
        35

<210> SEQ ID NO 43
<211> LENGTH: 39
<212> TYPE: PRT
<213> ORGANISM: Artificial Sequence
<220> FEATURE:
<223> OTHER INFORMATION: oxyntomodulin derivative
```

```
<220> FEATURE:
<221> NAME/KEY: VARIANT
<222> LOCATION: (1)
<223> OTHER INFORMATION: Xaa = 4-imidazoacetyl.

<400> SEQUENCE: 43

Xaa Gly Gln Gly Thr Phe Thr Ser Asp Tyr Ser Arg Tyr Leu Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 44
<211> LENGTH: 39
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.

<400> SEQUENCE: 44

Xaa Gly Gln Gly Thr Phe Thr Ser Asp Tyr Ser Arg Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 45
<211> LENGTH: 42
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.

<400> SEQUENCE: 45

Xaa Gly Glu Gly Thr Phe Thr Ser Asp Leu Ser Arg Gln Met Glu Glu
 1               5                  10                  15

Glu Ala Val Arg Leu Phe Ile Glu Trp Ala Ala His Ser Gln Gly Thr
            20                  25                  30

Phe Thr Ser Asp Tyr Ser Lys Tyr Leu Asp
        35                  40

<210> SEQ ID NO 46
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.
```

-continued

<400> SEQUENCE: 46

Xaa Ser Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys
            20                  25                  30

<210> SEQ ID NO 47
<211> LENGTH: 29
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.

<400> SEQUENCE: 47

Xaa Ser Gln Gly Thr Phe Thr Ser Asp Leu Ser Arg Gln Leu Glu Glu
1               5                   10                  15

Glu Ala Val Arg Leu Phe Ile Glu Trp Leu Met Asn Lys
            20                  25

<210> SEQ ID NO 48
<211> LENGTH: 37
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.
<220> FEATURE:
<221> NAME/KEY: VARIANT
<222> LOCATION: (20)
<223> OTHER INFORMATION: Xaa = alpha-methyl-glutamic acid

<400> SEQUENCE: 48

Xaa Gly Gln Gly Thr Phe Thr Ser Asp Tyr Ser Arg Tyr Leu Asp Glu
1               5                   10                  15

Glu Ala Val Xaa Leu Phe Ile Glu Trp Leu Met Asn Thr Lys Arg Asn
            20                  25                  30

Arg Asn Asn Ile Ala
        35

<210> SEQ ID NO 49
<211> LENGTH: 40
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.

<400> SEQUENCE: 49

Xaa Ser Gln Gly Thr Phe Thr Ser Asp Tyr Ser Arg Gln Met Glu Glu
1               5                   10                  15

Glu Ala Val Arg Leu Phe Ile Glu Trp Leu Met Asn Gly Gly Pro Ser
            20                  25                  30

Ser Gly Ala Pro Pro Pro Ser Lys
        35                  40

```
<210> SEQ ID NO 50
<211> LENGTH: 43
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.

<400> SEQUENCE: 50

Xaa Gly Glu Gly Thr Phe Thr Ser Asp Leu Ser Arg Gln Met Glu Glu
 1               5                  10                  15

Glu Ala Val Arg Leu Phe Ile Glu Trp Ala Ala His Ser Gln Gly Thr
            20                  25                  30

Phe Thr Ser Asp Tyr Ser Arg Tyr Leu Asp Lys
        35                  40

<210> SEQ ID NO 51
<211> LENGTH: 38
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.

<400> SEQUENCE: 51

Xaa Ser Gln Gly Thr Phe Thr Ser Asp Tyr Ser Arg Tyr Leu Asp Gly
 1               5                  10                  15

Gly Gly His Gly Glu Gly Thr Phe Thr Ser Asp Leu Ser Lys Gln Met
            20                  25                  30

Glu Glu Glu Ala Val Lys
        35

<210> SEQ ID NO 52
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.
<220> FEATURE:
<221> NAME/KEY: VARIANT
<222> LOCATION: (16)
<223> OTHER INFORMATION: Xaa = alpha-methyl-glutamic acid
<220> FEATURE:
<221> NAME/KEY: VARIANT
<222> LOCATION: (20)
<223> OTHER INFORMATION: Xaa = alpha-methyl-glutamic acid

<400> SEQUENCE: 52

Xaa Ser Gln Gly Thr Phe Thr Ser Asp Tyr Ser Arg Tyr Leu Asp Xaa
 1               5                  10                  15

Glu Ala Val Xaa Leu Phe Ile Glu Trp Leu Met Asn Thr Lys
            20                  25                  30

<210> SEQ ID NO 53
<211> LENGTH: 37
<212> TYPE: PRT
<213> ORGANISM: Artificial Sequence
```

```
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.
<220> FEATURE:
<221> NAME/KEY: VARIANT
<222> LOCATION: (20)
<223> OTHER INFORMATION: Xaa = alpha-methyl-glutamic acid
<220> FEATURE:
<221> NAME/KEY: VARIANT
<222> LOCATION: (24)
<223> OTHER INFORMATION: Xaa = alpha-methyl-glutamic acid

<400> SEQUENCE: 53

Xaa Gly Gln Gly Thr Phe Thr Ser Asp Tyr Ser Arg Tyr Leu Asp Glu
 1               5                  10                  15

Glu Ala Val Xaa Leu Phe Ile Xaa Trp Leu Met Asn Thr Lys Arg Asn
            20                  25                  30

Arg Asn Asn Ile Ala
        35

<210> SEQ ID NO 54
<211> LENGTH: 37
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.
<220> FEATURE:
<221> NAME/KEY: VARIANT
<222> LOCATION: (24)
<223> OTHER INFORMATION: Xaa = alpha-methyl-glutamic acid

<400> SEQUENCE: 54

Xaa Gly Gln Gly Thr Phe Thr Ser Asp Tyr Ser Arg Tyr Leu Asp Glu
 1               5                  10                  15

Glu Ala Val Arg Leu Phe Ile Xaa Trp Leu Met Asn Thr Lys Arg Asn
            20                  25                  30

Arg Asn Asn Ile Ala
        35

<210> SEQ ID NO 55
<211> LENGTH: 34
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.

<400> SEQUENCE: 55

Xaa Ser Gln Gly Thr Phe Thr Ser Asp Leu Ser Arg Gln Leu Glu Gly
 1               5                  10                  15

Gly Gly His Ser Gln Gly Thr Phe Thr Ser Asp Leu Ser Arg Gln Leu
            20                  25                  30

Glu Lys
```

```
<210> SEQ ID NO 56
<211> LENGTH: 37
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.

<400> SEQUENCE: 56

Xaa Ser Gln Gly Thr Phe Thr Ser Asp Tyr Ser Arg Tyr Leu Asp Glu
 1               5                  10                  15

Glu Ala Val Arg Leu Phe Ile Glu Trp Ile Arg Asn Thr Lys Arg Asn
            20                  25                  30

Arg Asn Asn Ile Ala
        35

<210> SEQ ID NO 57
<211> LENGTH: 40
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.

<400> SEQUENCE: 57

Xaa Ser Gln Gly Thr Phe Thr Ser Asp Tyr Ser Arg Tyr Leu Asp Glu
 1               5                  10                  15

Glu Ala Val Arg Leu Phe Ile Glu Trp Ile Arg Asn Gly Gly Pro Ser
            20                  25                  30

Ser Gly Ala Pro Pro Pro Ser Lys
        35                  40

<210> SEQ ID NO 58
<211> LENGTH: 37
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.
<220> FEATURE:
<221> NAME/KEY: VARIANT
<222> LOCATION: (16), (20)
<223> OTHER INFORMATION: amino acids at position 16 and position 20 form
     a ring

<400> SEQUENCE: 58

Xaa Ser Gln Gly Thr Phe Thr Ser Asp Tyr Ser Arg Tyr Leu Asp Glu
 1               5                  10                  15

Glu Ala Val Lys Leu Phe Ile Glu Trp Ile Arg Asn Thr Lys Arg Asn
            20                  25                  30

Arg Asn Asn Ile Ala
        35

<210> SEQ ID NO 59
<211> LENGTH: 40
<212> TYPE: PRT
<213> ORGANISM: Artificial Sequence
```

```
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 59

Xaa Ser Gln Gly Thr Phe Thr Ser Asp Tyr Ser Arg Tyr Leu Asp Glu
 1               5                  10                  15

Glu Ala Val Lys Leu Phe Ile Glu Trp Ile Arg Asn Gly Gly Pro Ser
                20                  25                  30

Ser Gly Ala Pro Pro Pro Ser Lys
            35                  40

<210> SEQ ID NO 60
<211> LENGTH: 37
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.

<400> SEQUENCE: 60

Xaa Ser Gln Gly Thr Phe Thr Ser Asp Tyr Ser Arg Gln Leu Glu Glu
 1               5                  10                  15

Glu Ala Val Arg Leu Phe Ile Glu Trp Val Arg Asn Thr Lys Arg Asn
                20                  25                  30

Arg Asn Asn Ile Ala
            35

<210> SEQ ID NO 61
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = desamino-histidyl.
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 61

Xaa Ser Gln Gly Thr Phe Thr Ser Asp Tyr Ser Lys Tyr Leu Asp Glu
 1               5                  10                  15

Lys Arg Ala Lys Glu Phe Val Gln Trp Leu Met Asn Thr Lys
                20                  25                  30

<210> SEQ ID NO 62
<211> LENGTH: 29
<212> TYPE: PRT
<213> ORGANISM: Artificial Sequence
<220> FEATURE:
<223> OTHER INFORMATION: oxyntomodulin derivative
```

```
<220> FEATURE:
<221> NAME/KEY: VARIANT
<222> LOCATION: (2)
<223> OTHER INFORMATION: Xaa = aminoisobutyric acid

<400> SEQUENCE: 62

His Xaa Gln Gly Thr Phe Thr Ser Asp Tyr Ser Lys Tyr Leu Asp Glu
 1               5                  10                  15

Lys Arg Ala Lys Glu Phe Val Cys Trp Leu Met Asn Thr
            20                  25

<210> SEQ ID NO 63
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (2)
<223> OTHER INFORMATION: Xaa = aminoisobutyric acid

<400> SEQUENCE: 63

His Xaa Gln Gly Thr Phe Thr Ser Asp Tyr Ser Lys Tyr Leu Asp Glu
 1               5                  10                  15

Lys Arg Ala Lys Glu Phe Val Gln Trp Leu Met Asn Thr Cys
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (2)
<223> OTHER INFORMATION: Xaa = aminoisobutyric acid
<220> FEATURE:
<221> NAME/KEY: VARIANT
<222> LOCATION: (12), (16)
<223> OTHER INFORMATION: amino acids at position 12 and position 16 form
      a ring

<400> SEQUENCE: 64

His Xaa Gln Gly Thr Phe Thr Ser Asp Tyr Ser Lys Tyr Leu Asp Glu
 1               5                  10                  15

Lys Arg Ala Lys Glu Phe Val Gln Trp Leu Met Asn Thr Cys
            20                  25                  30

<210> SEQ ID NO 65
<211> LENGTH: 29
<212> TYPE: PRT
<213> ORGANISM: Artificial Sequence
<220> FEATURE:
<223> OTHER INFORMATION: oxyntomodulin derivative'
<220> FEATURE:
<221> NAME/KEY: VARIANT
<222> LOCATION: (2)
<223> OTHER INFORMATION: Xaa = aminoisobutyric acid
<220> FEATURE:
<221> NAME/KEY: VARIANT
<222> LOCATION: (16), (20)
<223> OTHER INFORMATION: amino acids at position 16 and position 20 form
      a ring
```

```
<400> SEQUENCE: 65

His Xaa Gln Gly Thr Phe Thr Ser Asp Tyr Ser Lys Tyr Leu Asp Glu
 1               5                  10                  15

Gln Ala Ala Lys Glu Phe Ile Cys Trp Leu Met Asn Thr
            20                  25

<210> SEQ ID NO 66
<211> LENGTH: 29
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (2)
<223> OTHER INFORMATION: Xaa = aminoisobutyric acid

<400> SEQUENCE: 66

His Xaa Gln Gly Thr Phe Thr Ser Asp Tyr Ser Lys Tyr Leu Asp Glu
 1               5                  10                  15

Lys Arg Ala Lys Glu Phe Val Gln Trp Leu Met Asn Thr
            20                  25

<210> SEQ ID NO 67
<211> LENGTH: 37
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (2)
<223> OTHER INFORMATION: Xaa = d-serine.

<400> SEQUENCE: 67

His Xaa Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 68
<211> LENGTH: 37
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl

<400> SEQUENCE: 68

Xaa Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 69
<211> LENGTH: 37
<212> TYPE: PRT
<213> ORGANISM: Artificial Sequence
```

```
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl
<220> FEATURE:
<221> NAME/KEY: VARIANT
<222> LOCATION: (2)
<223> OTHER INFORMATION: Xaa = d-serine.

<400> SEQUENCE: 69

Xaa Xaa Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 70
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (1)
<223> OTHER INFORMATION: Xaa = 4-imidazoacetyl.
<220> FEATURE:
<221> NAME/KEY: VARIANT
<222> LOCATION: (2)
<223> OTHER INFORMATION: Xaa = aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 70

Xaa Xaa Gln Gly Thr Phe Thr Ser Asp Tyr Ser Lys Tyr Leu Asp Glu
 1               5                  10                  15

Lys Arg Ala Lys Glu Phe Val Gln Trp Leu Met Asn Thr Cys
            20                  25                  30

<210> SEQ ID NO 71
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (2)
<223> OTHER INFORMATION: Xaa = aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 71

His Xaa Gln Gly Thr Phe Thr Ser Asp Tyr Ala Lys Tyr Leu Asp Glu
 1               5                  10                  15

Lys Arg Ala Lys Glu Phe Val Gln Trp Leu Met Asn Thr Cys
            20                  25                  30
```

```
<210> SEQ ID NO 72
<211> LENGTH: 30
<212> TYPE: PRT
<213> ORGANISM: Artificial Sequence
<220> FEATURE:
<223> OTHER INFORMATION: oxyntomodulin derivative
<220> FEATURE:
<221> NAME/KEY: VARIANT
<222> LOCATION: (2)
<223> OTHER INFORMATION: Xaa = aminoisobutyric acid
<220> FEATURE:
<221> NAME/KEY: VARIANT
<222> LOCATION: (16), (20)
<223> OTHER INFORMATION: amino acids at position 16 and position 20 form
      a ring

<400> SEQUENCE: 72

Tyr Xaa Gln Gly Thr Phe Thr Ser Asp Tyr Ser Lys Tyr Leu Asp Glu
 1               5                  10                  15

Lys Arg Ala Lys Glu Phe Val Gln Trp Leu Met Asn Thr Cys
             20                  25                  30
```

METHOD FOR TREATING DIABETES MELLITUS BY A COMPOSITION COMPRISING INSULIN AND A GLP-1/GLUCAGON DUAL AGONIST

CROSS REFERENCE TO RELATED APPLICATIONS

This application is a National Stage of International Application No. PCT/KR2015/005455, filed Jun. 1, 2015, claiming priority based on Korean Patent Application No. 10-2014-0066554, filed May 30, 2014, the contents of all of which are incorporated herein by reference in their entirety.

TECHNICAL FIELD

The present invention relates to a composition for treating diabetes mellitus including insulin and a GLP-1/glucagon dual agonist, and a method for preventing or treating diabetes mellitus, including administering the composition.

BACKGROUND ART

Insulin is a peptide secreted from pancreatic beta cells, which plays an important role in the regulation of blood sugar in the body. Diabetes mellitus is a kind of a metabolic disease in which insulin secretion is insufficient or normal functions are not made, which leads to increased blood glucose levels. Type 2 diabetes is the case in which insulin is not secreted properly or the secreted insulin is not properly processed in the body and the blood glucose levels are not controlled and so are raised. Type 2 diabetes is conventionally treated using a hypoglycemic agent containing a chemical material as an active ingredient or, for some patients, treated by administration of insulin. On the other hand, in Type 1 diabetes, the administration of insulin is essentially required.

Insulin therapy, which is currently widely used, is a method of administering insulin via injection before and after meals. Insulin is now available as an injection and is principally administered by subcutaneous injection, and the method of administration is different according to the action time. Insulin administration appears a more quick hypoglycemic effect than the drugs taken, and can be safely used even in environments in which the drugs are not available. Further, there is no limitation on the amount of the dose, but the administration of insulin must occur three times a day. Therefore, there are disadvantages such as patient fear of needles, the difficulty of administration, hypoglycemia symptoms, and weight gain due to long-term administration of insulin. The weight gain increases the risk of cardiovascular disease, which can lead to the side effect of lowered blood sugar control function.

A dual agonist capable of binding to both GLP-1 and two peptide glucagon receptors is currently being studied as a mechanism to concurrently treat both diabetes and obesity. The GLP-1 and the glucagon dual agonist inhibit food intake of GLP-1, promote satiety, show lipolytic function of glucagon, maintain blood sugar reduction and show a high effect on reducing body weight, thereby having high possibility of use as new therapeutic agents.

The present inventors have found that insulin and the dual agonist are inconvenient in that administration must be made daily to the patient due to a short half-life, and have suggested, as a technique of maintaining the activity of protein drug and achieving improved stability at the same time in order to solve the abovementioned problems, a long-acting protein conjugate in which a conventional physiologically active polypeptide and an immunoglobulin Fc region are covalently combined with each other by a non-peptidyl polymer linker (Korean Patent No. 10-0725315). In particular, the inventors have confirmed that the sustainability of the in vivo effects of both the long-acting insulin conjugate and long-acting dual agonist conjugate is dramatically increased (Korean Patent No. 10-1058290, Korean Patent Application No. 10-2014-0022909 and Korean Patent Application Publication No. 10-2012-0139579).

However, there are problems in that side-effects such as weight gain occur upon administration of GLP-1/glucagon dual agonist. Therefore, there still remains a need for the development of a therapeutic agent for diabetes having reduced side-effects, frequency and dosage

DISCLOSURE

Technical Problem

The present inventors have made many efforts to develop a therapeutic agent for diabetes which can reduce high blood glucose levels, suppress weight gain, and reduce the risk of hypoglycemia, which are required to treat diabetes. As a result, the present inventors have attempted a combined administration which simultaneously administers an insulin receptor and GLP-1/glucagon dual agonist, and specifically discovered that when a combined administration of a long-acting insulin and long-acting GLP-1/glucagon can maximize compliance of the patient, reduce the dosage of the insulin drug, reduce the risk of hypoglycemia, and help to reduce blood glucose level and body weight, thereby completing the present invention.

Technical Solution

An objective of the present invention is to provide a composition for treating diabetes mellitus including insulin and a GLP-1/glucagon dual agonist.

Another objective of the present invention is to provide a method for preventing or treating diabetes, including administering the composition to a subject at high risk of or having diabetes mellitus.

Advantageous Effects

The long-acting insulin or its analog conjugate and a long-acting GLP-1/glucagon agonist conjugate exhibit an excellent therapeutic effect on diabetes, and particularly combined administration is effective as a therapeutic agent for diabetes which can concurrently stimulate two peptide receptors of the insulin receptor and GLP-1 and glucagon to improve the in vivo sustainability and stability, dramatically reduce the administration dosage, reduce hypoglycemia and weight gain due to stable control of blood glucose levels and has drug compliance. In particular, the present invention can dramatically improve stability in blood, has a sustainable drug effect and lowers the administration frequency, thereby maximizing patient convenience.

DESCRIPTION OF DRAWINGS

FIG. 1 is an AUC (area under the curve) graph showing the fasting glucose change measured while a long-acting GLP/glucagon dual agonist-immunoglobulin Fc conjugate and an insulin analog-Fc conjugate were subcutaneously administered to the db/db mice once every two days for 4 weeks via a single administration or combined administration.

FIG. 2 is a graph showing the body weight change measured before and after a long-acting GLP/glucagon dual agonist-immunoglobulin Fc conjugate and an insulin analog-Fc conjugate were subcutaneously administered to the db/db mice once every two day for 4 weeks via a single administration or combined administration.

BEST MODE

In order to accomplish the above-described objects, in an aspect, the present invention provides a composition for treating diabetes mellitus including insulin and a GLP-1/glucagon dual agonist.

The insulin above is a long-acting conjugate in which insulin and a biocompatible material or a carrier are linked by a covalent bond or a linker. The GLP-1/glucagon dual agonist is a long-acting GLP-1/glucagon dual agonist and may be a long-acting GLP-1/glucagon dual agonist conjugate in which the GLP-1/glucagon dual agonist and a biocompatible material or a carrier are linked by a covalent bond or a linker. The composition of the present invention is characterized by a combined administration of insulin and GLP-1/glucagon dual agonist. The insulin and GLP-1/glucagon dual agonist of the present invention are characterized by a long-acting type.

In the composition of the present invention, a mole ratio of GLP-1/glucagon dual agonist:insulin may range from 1:0.05 to 1:50, but is not limited thereto as long as it shows the effect of the present invention. Preferably, the insulin and GLP-1/glucagon dual agonist are a long-acting type, and may be in the form of a conjugate in which a biocompatible material or a carrier is linked.

In the present invention, the insulin includes all peptides or modified peptides which have a stimulating effect on insulin receptors. For example, the insulin may be a native insulin, a rapid-acting insulin, a basal insulin, an insulin analog which is a material prepared by any one of substitution, addition, deletion, and modification, or may be a combination of some amino acids of native insulin, or may be a fragment thereof. Also, in the present invention, insulin may be a long-acting insulin employing long-acting techniques to overcome the short half-life. Preferably, it may be a long-acting insulin or a long-acting insulin analog which can be administered once a week. Some specific examples of the insulin according to the present invention include insulin or insulin analog and its long-acting type as described in Korean Patent No. 10-1058290, and Korean Patent Application Nos. 10-2014-0022909 and 10-2014-0006938, but are not limited thereto.

As used herein, the term □insulin analogue□ refers to a peptide having change of one or more amino acids of a native sequence.

The insulin analog may be an insulin analog in which A-chain or B-chain amino acid of insulin is changed, having reduced insulin threshold and reduced insulin receptor binding affinity as compared with a wild-type. The native insulin amino acid sequences are as follows.

```
A chain:
                                           (SEQ ID NO: 37)
Gly-Ile-Val-Glu-Gln-Cys-Cys-Thr-Ser-Ile-Cys-Ser- Leu-Tyr-Gln-Leu-Glu-Asn-Tyr-Cys-Asn B chain:
                                           (SEQ ID NO: 38)
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

Although the insulin used in the embodiment of the invention is an insulin analog prepared by a genetic recombination, the present invention is not limited thereto. Preferably, the insulin includes inverted insulin, insulin variants, insulin fragments, etc., and the preparation method thereof includes gene recombination as well as a solid phase method, but is not limited thereto.

The insulin analog is a peptide having a blood glucose control functionality in vivo which is the same as that of insulin. Such a peptide includes insulin agonists, derivatives, fragments, mutants and the like.

The insulin agonist of the present invention refers to a material that exhibits the same biological activity as insulin by binding to the insulin receptor in vivo, regardless of the structure of insulin.

The insulin analog of the present invention shows a amino acid sequence homology with A-chain and B-chain of native insulin, respectively, and at least one amino acid residue may be an altered form selected from the group consisting of substitution (e.g.; alpha-methylation, alpha-hydroxylation), deletion (e.g., deamination) or modification (e.g., N-methylation), and a combination thereof, and it may refer to a peptide capable of controlling the blood glucose level.

As used herein, the insulin analog may refer to a peptide mimic and a low-molecular or a polymer compound which can be linked to an insulin receptor to control blood glucose levels, although a native insulin and an amino acid sequence have no homology.

The insulin fragment of the present invention refers to a fragment having one or more amino acids added or deleted in insulin. The added amino acid can be an amino acid that is not present in a native state (e.g., D-type amino acid). Such an insulin fragment has a function to control blood glucose levels.

The insulin variant of the present invention refers to a peptide having one or more amino acid sequences different from those of insulin, and having a function to control blood glucose levels in the body.

Methods for preparing the insulin agonist, derivative, fragment and variant may be used alone or in combination. For example, the present invention includes a peptide, which has one or more amino acids different from those of native peptide, has deamination of the terminal amino acid residue, and has a function to control blood glucose levels in the body.

Specifically, the insulin analog may be that in which one or more amino acids selected from the group consisting of amino acids at position 1, amino acids at position 2, amino acids at position 3, amino acids at position 5, amino acids at position 8, amino acids at position 10, amino acids at position 12, amino acids at position 16, amino acids at position 23, amino acids at position 24, amino acids at position 25, amino acids at position 26, amino acids at position 27, amino acids at position 28, amino acids at position 29, amino acids at position 30 of the chain B; amino acids at position 5, amino acids at position 8, amino acids at position 10, amino acids at position 12, amino acids at position 14, amino acids at position 16, amino acids at position 17, amino acids at position 18, amino acids at position 19 and amino acids at position 21 of the chain A have been substituted with other amino acids, and preferably those substituted with alanine, glutamic acid, asparagine, isoleucine, valine, glutamine, glycine, lysine, histidine, cysteine, phenylalanine, tryptophan, proline, serine, threonine, or aspartic acids. In addition, an insulin analog having a deletion of at least one amino acid is included within the scope of the present invention, but any insulin analog may be included without limitation.

The preferred insulin analog is an insulin analog which is combined with biocompatible material or a carrier to have increased half-life as compared to the wild-type insulin, and this may be the insulin analog described in Korean Patent Application Nos. 10-2014-0022909 and 10-2014-0006938, but is not limited thereto.

In the present invention, the GLP-1/glucagon dual agonist includes all peptides or fragments, precursors, variants or derivatives thereof which have GLP-1/glucagon dual activity, like oxyntomodulin, a native GLP-1/glucagon dual agonist. In the present invention, the GLP-1/glucagon dual agonist may be a GLP-1/glucagon dual agonist employing the long-acting technique to overcome the short half-life, and preferably a long-acting GLP-1/glucagon dual agonist which can be administered once a week. Specific examples of the GLP-1/glucagon dual agonist according to the present invention partially include, for example, the GLP-1/glucagon dual agonist and a derivative thereof and a long-acting type thereof as described in Korean Patent Application Publication Nos. 10-2012-0137271 and 10-2012-0139579, the entire contents of which are incorporated herein by reference.

As used herein, the term "oxyntomodulin" means a peptide derived from a glucagon precursor, pre-glucagon, and includes a native oxyntomodulin, precursors, derivatives, fragments thereof, and variants thereof. Preferably, it can have the amino acid sequence of SEQ ID NO. 39 (HSQGTFTSDYSKYLDSRRAQDFVQWLMNTKRNRNNIA).

The term, "oxyntomodulin variant" is a peptide having one or more amino acid sequences different from those of native oxyntomodulin, and means a peptide that retains the function of activating the GLP-1 and glucagon receptors, and it may be prepared by any one of substitution, addition, deletion, and modification or by a combination thereof in a part of the amino acid sequences of the native oxyntomodulin.

The term, "oxyntomodulin derivative" includes peptides, peptide derivatives or peptide mimetics that are prepared by addition, deletion or substitution of amino acids of oxyntomodulin so as to activate both of the GLP-1 receptor and the glucagon receptor at a high level, compared to the native oxyntomodulin. Preferably, the oxyntomodulin derivative has an amino acid sequence of SEQ ID No. 40 and more preferably, its $16^{th}$ and $20^{th}$ amino acids form a ring.

The term, "oxyntomodulin fragment" means a fragment having one or more amino acids added or deleted at the N-terminus or the C-terminus of the native oxyntomodulin, in which non-naturally occurring amino acids (for example, D-type amino acid) can be added, and has a function of activating both of the GLP-1 receptor and the glucagon receptor.

Each of the preparation methods for the variants, derivatives, and fragments of oxyntomodulin can be used individually or in combination. For example, the present invention includes a peptide that has one or more amino acids different from those of native peptide and deamination of the N-terminal amino acid residue, and has a function of activating both of the GLP-1 receptor and the glucagon receptor.

In an embodiment of the present invention, the long-acting type of the insulin and GLP-1/glucagon dual agonist may be in a conjugate form, wherein a biocompatible material or a carrier is linked to the insulin or dual agonist by a covalent bond or a linker. In another embodiment, such long-acting type may be in a form, wherein a biocompatible material or a carrier cannot be linked directly to the insulin or dual agonist by a covalent bond. The long-acting type of the aforementioned insulin or GLP-1/glucagon dual agonist can improve the half-life or bioavailability as compared with a form in which the sequence of the insulin or dual agonist is not the long-acting type but is otherwise the same. In accordance with one embodiment of the present invention, the long-acting insulin is in a form wherein the immunoglobulin Fc region are linked to the insulin analog in which amino acids at position 14 of the insulin chain A is substituted with glutamic acids, via the non-peptidyl polymer as a linker. The long-acting GLP-1/glucagon dual agonist may be a composition in which the immunoglobulin Fc region is linked to amino acids at position 30 of the GLP-1/glucagon dual agonist by the non-peptidyl polymer as a linker, but is not limited thereto.

The present inventors have found that the combined administration of insulin and GLP-1/glucagon dual agonist can prevent weight gain associated with a single administration of insulin, the risk of hypoglycemia can be reduced by reducing the amount of insulin, and further in order to exhibit more excellent effect of reduction of blood glucose levels than that of a single administration of the dual agonist, the combined administration of the two drugs can reduce side-effects and increase the effects as compared with the single administration of each drug. The inventors have also confirmed that the composition for combined administration can be used as effective therapeutic agents while reducing side-effects of conventional therapeutic agent of diabetes.

As used herein, the term "biocompatible material" or "carrier" refer to materials which can increase the duration of the activity of the insulin or insulin analog or GLP-1/glucagon dual agonist when the biocompatible material and the carrier are covalently or non-covalently linked to the insulin or insulin analog or GLP-1/glucagon dual agonist of the present invention directly or indirectly to form a conjugate. For example, when forming the conjugate, a material which can increase the in vivo half-life of the insulin or insulin analog or GLP-1/glucagon dual agonist may be a biocompatible material or carrier according to the present invention. The type of the biocompatible material or carrier that can be used to increase the half-life varies, and examples thereof include polyethylene glycol, fatty acid, cholesterol, albumin and fragment thereof, albumin-binding substance, a polymer of repeating units of a specific amino acid sequence, antibodies, antibody fragments, Fc neonatal receptor (FcRn) binding materials, in vivo connective tissue, nucleotides, fibronectin, transferrin, saccharide, polymers, and the like. Of course, they may be used in combination of two or more of the aforementioned carrier or biocompatible material. The biocompatible material or carrier includes a biocompatible material that extends the in vivo half life through a covalent or non-covalent bond.

In the present invention, the methods in which the biocompatible material or the carrier are linked to the insulin or dual agonist include a genetic recombination method and an in vivo connection using polymers or low molecular weight chemicals, but are not limited thereto. The FcRn binding material may be an immunoglobulin Fc region. For example, when polyethylene glycol is used as the carrier, there may be included a Recode technique by Ambrx Inc. which can attach position-specifically to polyethylene glycol. There can also be included a glycopegylation technique by Neose company which can attach specifically to the glycosylated moiety. Furthermore, there can be included a releasable PEG technique in which polyethylene glycol is deleted, but is not limited thereto. There may be included techniques which increase bioavailability using PEG. In addition, there can be included polymers such as polyethylene glycol, polypropylene glycol, ethylene glycol-propylene glycol copolymer, polyoxyethylated polyol, polyvinyl alcohol, polysaccharides, dextran, polyvinyl ethyl ether, biodegradable polymer, lipid polymer, chitins, or hyaluronic acid.

When using the albumin as a carrier, there can be included a technique in which albumins or albumin fragments can be directly covalently linked to peptides of the insulin to increase the in vivo stability. Even if albumin is not directly linked, there may be included a technique in which the albumin binding materials, for example, albumin-specific binding antibody or antibody fragment are bound to the peptides to bind to the albumin, and a technique in which a certain peptide/protein having a binding affinity to albumin is bound to the peptides. In addition, there may be included a technique in which a fatty acid having a binding affinity to albumin is bound to the peptides, but is not limited thereto. Any technique or binding method which can increase the in vivo stability using albumin can be included here.

The technique for binding to the peptide using the antibody or antibody fragment as a carrier in order to increase the in vivo half-life may also be included in the present invention. The antibody or antibody fragment having a FcRn binding site can be used, and any antibody fragment containing no FcRn binding site such as Fab can be used. CovX-body technique of CovX company using a catalytic antibody can be included herein, and the technique which increases the in vivo half-life using Fc fragments can be included in the present invention. When using the Fc fragment, the linker binding to the Fc fragment and the peptide and its binding method may include a peptide bond or a polyethylene glycol or the like, but is not limited to thereto and any chemical binding method is available. In addition, the binding ratio of the Fc fragment and the insulin of the present invention may be 1:1 or 1:2, but is not limited thereto.

The technique in which peptides or protein fragments are used as carriers to link to insulin analog can be included in the present invention in order to increase the in vivo half-life. The peptides or protein fragments used may be Elastin like polypeptide (ELP) which is composed of the repeating units of a combination of a certain amino acid. The artificial polypeptide PEG Xten technique of Versartis company is included in the present invention. In addition, the structure inducing probe (SIP) technique of Zealand company, which increases the in vivo half-life using multi-Lysine, is also included in the present invention. The fusion technique of Prolor company is included herein. Transferrin known to have a high in vivo stability or fibronectin and derivatives thereof which are a component of connective tissue can be included herein. The peptides or proteins which are bound to the insulin of the present invention are not limited thereto, and any peptides or proteins which increase the in vivo half-life of insulin are include in the scope of the present invention. Linking of the insulin of the present invention and the peptides or proteins increasing the in vivo half-life may be by a covalent bond. The types of linker and the binding method used may be a peptide binding or polyethylene glycol and the like, but are not limited thereto, and any chemical linking method is also possible.

Further, the carrier which is used to increase the in vivo half-life may be a non-peptidyl material such as a polysaccharide or a fatty acid.

The linker binding to the carrier which is used to increase the in vivo half-life may include peptides, polyethylene glycols, fatty acids, sugars, polymers, low molecular weight compounds, nucleotides and a combination thereof, and may be any chemical bond such as a non-covalent chemical bond or a covalent chemical bond, without limitation.

The formulation which can increase the bioavailability or continuously maintain the activity may include a sustained release formulation by microparticles, nanoparticles and the like using PLGA, hyaluronic acid, chitosan, etc.

Furthermore, the formulation of different aspects which can increase the bioavailability or continuously maintain the activity may be a formulation such as implants, inhalants, transnasal formulations or patches.

In one exemplary embodiment of the invention, examples of insulin administered in combination with the GLP-1/glucagon dual agonist may include a native insulin, an insulin analog, a long-acting insulin and the like (e.g., a native insulin such as Humulin, Novolin, a rapid-acting insulin such as Novolog, Humalog, Apidra, a long-acting insulin such as Lantus, Levemir, Tresiba may be included).

In another exemplary embodiment of the present invention, examples of GLP-1/glucagon dual agonist which can be administered in combination with the insulin or insulin analog and a long-acting formulation thereof may include a native GLP-1/glucagon dual agonist such as oxyntomodulin and a derivative thereof and a long-acting formulation thereof and the like.

The carrier material which can be used in the present invention can be selected from the group consisting of an antibody, an immunoglobulin Fc region, an albumin, a fatty acid, a carbohydrate, a polymer having a repeating unit of peptide, a transferrin, and a PEG, and preferably an immunoglobulin Fc region. In an exemplary embodiment of the present invention, the long-acting GLP-1/glucagon dual agonist is linked to a carrier by the non-peptidyl polymer as a linker. In a further exemplary embodiment, the carrier material linked to the non-peptidyl polymer linker is an immunoglobulin Fc fragment.

In the present invention, the long-acting insulin conjugate (or for brevity, insulin conjugate) or the long-acting GLP-1/glucagon dual agonist (for brevity, dual agonist conjugate) is a form in which the insulin or dual agonist is linked to an immunoglobulin Fc region, and exhibits sustainability and safety. Binding of the immunoglobulin Fc region and the insulin or dual agonist may be by an inframe fusion without a linker or may be linked using a non-peptide polymer as a linker. In the present invention, the immunoglobulin Fc may be used interchangeably with immunoglobulin fragments.

The term "non-peptidyl polymer" refers to a biocompatible polymer including two or more repeating units linked to each other by any covalent bond excluding a peptide bond. In the present invention, the non-peptidyl polymer may be interchangeably used with the non-peptidyl linker.

The non-peptidyl polymer useful in the present invention may be selected from the group consisting of a biodegradable polymer, a lipid polymer, chitin, hyaluronic acid, and a combination thereof. The biodegradable polymer may be polyethylene glycol, polypropylene glycol, ethylene glycol-propylene glycol copolymer, polyoxyethylatedpolyol, polyvinyl alcohol, polysaccharide, dextran, polyvinyl ethyl ether, polylactic acid (PLA) or polylactic-glycolic acid (PLGA), and preferably a polyethylene glycol. In addition, derivatives thereof known in the art and derivatives easily prepared by a method known in the art may be included in the scope of the present invention.

The peptide linker which is used in the fusion protein obtained by a conventional inframe fusion method has drawbacks in that it is easily cleaved in vivo by a proteolytic enzyme, and thus a sufficient effect of increasing the serum half-life of the active drug by a carrier cannot be obtained as expected. However, in the present invention, the polymer having resistance to the proteolytic enzyme can be used to maintain the serum half-life of a peptide being similar to that of the carrier. Therefore, any non-peptidyl polymer can be used in the present invention without limitation, as long as it is a polymer having the aforementioned function, that is, a polymer having resistance to the in vivo proteolytic enzyme. The non-peptidyl polymer has a molecular weight in the range of 1 to 100 kDa, and preferably of 1 to 20 kDa. The non-peptidyl polymer of the present invention, linked to the immunoglobulin Fc region, may be one type of polymer or a combination of different types of polymers. The non-peptidyl polymer used in the present invention has a reactive group capable of binding to the immunoglobulin Fc region and protein drug. The non-peptidyl polymer has a reactive group at both terminal ends, which is preferably selected from the group consisting of a reactive aldehyde group, a propionaldehyde group, a butyraldehyde group, a maleimide group and a succinimide derivative. The succinimide derivative may be succinimidyl propionate, hydroxy succinimidyl, succinimidyl carboxymethyl, or succinimidyl carbonate. In particular, when the non-peptidyl polymer has a reactive group of the reactive aldehyde group at both terminal ends thereof, it is effective in linking at both ends with a physiologically active polypeptide and an immunoglobulin with minimal non-specific reactions. A final product produced by reductive alkylation by an aldehyde bond is much more stable than that linked by an amide bond. The aldehyde reactive group selectively reacts at an N-terminus at a low pH, and binds to a lysine residue to form a covalent bond at a high pH, such as pH 9.0. The reactive groups at both terminal ends of the non-peptidyl polymer may be the same as or different from each other. For example, the non-peptidyl polymer may possess a maleimide group at one end, and an aldehyde group, a propionaldehyde group or a butyraldehyde group at the other end. When a polyethylene glycol having a reactive hydroxy group at both ends thereof is used as the non-peptidyl polymer, the hydroxy group may be activated to various reactive groups by known chemical reactions, or a polyethylene glycol having a commercially available modified reactive group may be used so as to prepare the long acting GLP-1/glucagon conjugate of the present invention.

In addition, the immunoglobulin Fc region is advantageous in terms of the preparation, purification, and yield of the conjugate because the molecular weight is relatively small as compared with the total molecular, as well as the homogeneity of the materials is greatly increased and the potential of inducing antigenicity in blood is lowered because the amino acid sequences are different for each antibody and the Fab portion showing a high non-homogeneity is deleted.

Further, the term "immunoglobulin Fc region" as used herein refers to the heavy-chain constant region 2 (CH2) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin. It may further include a hinge region at the heavy-chain constant region.

Also, the immunoglobulin Fc region of the present invention may contain a part or all of the Fc region including the heavy-chain constant region 1 (CH1) and/or the light-chain constant region 1 (CL1), except for the variable regions of the heavy and light chains of the immunoglobulin, as long as it has a physiological effect substantially similar to or better than the native protein. Furthermore, the immunoglobulin Fc region may be a fragment having a deletion in a relatively long portion of the amino acid sequence of CH2 and/or CH3. That is, the immunoglobulin Fc region of the present invention may include 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region. Further, the immunoglobulin Fc region of the present invention includes a native amino acid sequence as well as a sequence derivative (mutant) thereof. An amino acid sequence derivative has a different sequence due to a deletion, an insertion, a non-conservative or conservative substitution or combinations thereof of one or more amino acid residues of the native amino acid sequences. For example, in an IgG Fc, amino acid residues known to be important in binding, at positions 214 to 238, 297 to 299, 318 to 322, or 327 to 331, may be used as a suitable target for modification.

Further, various kinds of derivatives are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site and an ADCC (antibody dependent cell mediated cytotoxicity) site. Techniques of preparing such sequence derivatives of the immunoglobulin Fc region are disclosed in International Publications, WO97/34631 and WO 96/32478.

Amino acid exchanges in proteins and peptides, which do not entirely alter the activities of the molecules, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions. In addition, the Fc region, if desired, may be modified by phosphorylation, sulfation, acrylation, glycosylation, methylation, farnesylation, acetylation, amidation, and the like. The above-described Fc derivatives are derivatives that exhibit biological activities identical to the Fc region of the present invention or improved structural stability, for example, against heat, pH, etc., compared to the Fc region.

Furthermore, these Fc regions may be obtained from native forms isolated from humans and other animals including cattle, goats, pigs, mice, rabbits, hamsters, rats, or guinea pigs, or may be recombinants or derivatives thereof, obtained from transformed animal cells or microorganisms. Herein, they may be obtained from a native immunoglobulin by isolating whole immunoglobulins from human or animal organisms and then treating them with a proteolytic enzyme. Papain digests the native immunoglobulin into Fab and Fc regions, and pepsin treatment results in the production of pFc' and F(ab)2 fragments. These fragments may be subjected, for example, to size exclusion chromatography to isolate Fc or pFc' fragments. Preferably, a human-derived Fc region is a recombinant immunoglobulin Fc region obtained from a microorganism.

In addition, the immunoglobulin Fc region may be in the form of having native sugar chains, increased sugar chains compared to a native form or decreased sugar chains compared to the native form, or may be in a deglycosylated form. The increase, decrease, or removal of the immunoglobulin Fc sugar chains may be achieved by methods commonly used in the art, such as a chemical method, an enzymatic method and a genetic engineering method using a microorganism. The removal of sugar chains from an Fc region results in a sharp decrease in binding affinity to the Clq part of the first complement component C1 and a decrease or loss in antibody-dependent cell-mediated cytotoxicity or complement-dependent cytotoxicity, thereby not inducing unnecessary immune responses in vivo. In this regard, an immunoglobulin Fc region in a deglycosylated or aglycosylated form may be more suitable to the objective of the present invention as a drug carrier.

As used herein, the term "deglycosylation" refers to enzymatically removing sugar moieties from an Fc region, and the term "aglycosylation" means that an Fc region is produced in an unglycosylated form by a prokaryote, preferably E. coli.

Meanwhile, the immunoglobulin Fc region may be derived from humans or other animals including cattle, goats, pigs, mice, rabbits, hamsters, rats, and guinea pigs, and preferably from humans.

Also, the immunoglobulin Fc region may be an Fc region that is derived from IgG, IgA, IgD, IgE and IgM, or that is made by combinations thereof or hybrids thereof. Preferably, it is derived from IgG or IgM, which are among the most abundant proteins in human blood, and most preferably from IgG, which is known to enhance the half-lives of ligand-binding proteins, but is not limited thereto.

On the other hand, the term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

As used herein, the term "hybrid" means that a sequence corresponding to at least two Fc fragments of a different origin is present in a single-chain immunoglobulin Fc region. In the present invention, various types of hybrid are possible. That is, the hybrid consisting of 1 to 4 domains selected from the group consisting of CH1, CH2, CH3 and CH4 of IgG Fc, IgM Fc, IgA Fc, IgE Fc and IgD Fc is possible, and may include a hinge.

On the other hand, IgG can also be divided into sub-classes of IgG1, IgG2, IgG3 and IgG4, and in the present invention, a combination or hybridization thereof is possible. It is preferably sub-classes of IgG2 and IgG4, and most preferably Fc region of IgG4 that has a substantial effector function, such as a complement dependent cytotoxicity (CDC).

That is, the immunoglobulin Fc region for the carrier of the drug of the present invention may be, for example, human IgG4-derived aglycosylated Fc region, but is not limited thereto. The human-derived Fc region is preferable as compared to nonhuman-derived Fc region which can cause undesirable immune responses, for example, can act as an antigen in the human body to produce a new antibody.

The method for preparing a long-acting insulin of the present invention is not particularly limited. For example, details of the preparation method and its effects are described, for example, in Korean Patent Nos. 10-1330868, 10-1324828, 10-1058290, Korean Patent Application Publication No. 10-2011-0111267, and Korean Patent Application No. 10-2014-0022909.

In an embodiment of the present invention, the long-acting insulin analog conjugate was prepared by conducting mono-PEGylation at N-terminal of the immunoglobulin Fc region and modifying the same to phenyl alanine at position 1 of the insulin and insulin analog chain B (Example 8).

The method for preparing a long-acting GLP-1/glucagon dual agonist of the present invention is not particularly limited. For example, details of the preparation method and its effects are described, for example, in Korean Patent Application Publication No. 10-2012-0139579. In an embodiment of the present invention, the long-acting insulin analog conjugate was prepared by conducting mono-PEGylation at N-terminal of the immunoglobulin Fc region and modifying the same to cysteine residue at position 30 of the GLP-1/glucagon dual agonist.

In another aspect, the present invention provides a composition containing a long-acting insulin and a long-acting GLP-1/glucagon dual agonist conjugate.

When such long-acting insulin conjugate and a long-acting GLP-1/glucagon dual agonist are administered in combination thereof, the long-acting insulin conjugate acts on the insulin receptor and the GLP-1/glucagon dual agonist conjugate acts on the glucagon-like peptide-1 receptor and the glucagon receptor concurrently to reduce blood glucose levels as compared to a single administration of each of them and show a stable change progress. Also, a combined administration of the above-described conjugates can lower the danger of hypoglycemia which can appear upon single administration of insulin, and reduce the total insulin dosage by the insulin secretion peptide. Using the long-acting insulin conjugate and the long-acting GLP-1/glucagon dual agonist has big advantages in that the number of administrations to a chronic patient, who would otherwise needs daily administrations, can be dramatically reduced due to an increase in the blood half-life and in vivo sustainability, thereby improving the quality of life for the patient. Therefore, this is very effective in the treatment of diabetes. The pharmaceutical composition of the present invention has excellent in vivo sustainability and dose threshold and significantly reduces the dosage used in combined administration.

The long-acting insulin conjugate and the long-acting GLP-1/glucagon dual agonist conjugate may be simultaneously, sequentially, or reversely administered, and simultaneously administered in combination of a suitable effective amount. Also, preferably, the long-acting insulin conjugate and the long-acting GLP-1/glucagon dual agonist conjugate may be simultaneously, sequentially, or reversely administered after storage in separate containers.

The long-acting insulin conjugate and the long-acting GLP-1/glucagon dual agonist conjugate which are the composition for combined administration of the present invention may be in a form of a kit for treatment of diabetes which was either included in one container or stored in a separate container. Such kit can include a pharmaceutically acceptable carrier and an instruction for use of the kit.

In the present inventions, the term diabetes refers to metabolic diseases in which insulin secretion is insufficient or normal functions are not made, which is characterized by increased blood glucose levels. The combined administration of the composition of the present invention to a subject can control blood glucose levels to treat diabetes mellitus.

As used herein, the term "prevention" refers to all of the actions that inhibit or delay the diabetes by combined administration of the composition of the present invention. The "treatment" refers to all of the actions that alleviate, improve or ameliorate the symptoms of the diabetes by a combined administration of the composition of the present invention. The treatment of the diabetes is applicable to any mammal that may experience the diabetes mellitus, and examples thereof include not only humans and primates, but also cattle such as cow, pigs, sheep, horses, dogs, and cats, without limitation, and preferably humans.

As used herein, the term "administration" refers to introduction of an amount of a predetermined substance to a patient by a suitable method. The composition of the present invention may be administered via any of the common routes, as long as it is able to reach a desired tissue. For example, it may be intraperitoneal, intravenous, intramuscular, subcutaneous, intradermal, oral, topical, intranasal, intrapulmonary, or intrarectal administration, but is not limited thereto. However, since peptides are digested upon oral administration, active ingredients of a composition for oral administration should be coated or formulated for protection against degradation in the stomach. Preferably, the composition may be administered in the form of injections. In addition, the long-acting formulation may be administered by any apparatus in which an active material can be transported into a target cell.

The administration dose and frequency of the pharmaceutical composition of the present invention are determined by the type of active ingredient, together with various factors such as the disease to be treated, administration route, patient's age, gender, and body weight, and disease severity.

The pharmaceutical composition of the present invention may further include a pharmaceutically acceptable carrier. In the present invention, the term "pharmaceutically acceptable carrier" refers to a diluent or carrier that does not inhibit the biological activity and properties of the administered compound without stimulating the organism. For oral administration, the carrier may include a binder, a lubricant, a disintegrant, an excipient, a solubilizer, a dispersing agent, a stabilizer, a suspending agent, a colorant, and a flavoring agent. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

On the other hand, examples of the carrier, the excipient, and the diluent suitable for the pharmaceutical formulations include lactose, dextrose, sucrose, sorbitol, mannitol, xylitol, erythritol, maltitol, starch, acacia rubber, alginate, gelatin, calciumphosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

In another aspect, the present invention provides a method for preventing or treating diabetes, including administering the composition containing insulin and a GLP-1/glucagon dual agonist to a subject at high risk of or having the diabetes mellitus.

The composition and non-alcoholic fatty liver disease are the same as described above.

In another aspect, the present invention provides a method for preventing or treating diabetes, including administering the composition containing insulin and a GLP-1/glucagon dual agonist to a subject at high risk of or having diabetes mellitus.

The composition and non-alcoholic fatty liver disease are the same as described above.

The administering step can be performed by combined administration of the long-acting insulin conjugate and the long-acting GLP-1/glucagon dual agonist conjugate, but is not limited thereto. Each of them may be simultaneously, sequentially, or reversely administered, and can be simultaneously administered in an appropriate effective amount.

The composition of the present invention including both a long-acting insulin conjugate and a long-acting GLP-1/glucagon dual agonist conjugate can greatly reduce blood glucose levels and has no side-effects of weight gain, although they are administered once a week, and thus, can be used in the prevention and treatment of diabetes.

MODE FOR INVENTION

Hereinafter, the present invention will be described in more detail by way of examples. These examples are only intended to illustrate the present invention, and the scope of the present invention is not construed as being limited to these examples.

Example 1

Production of the Single-Chain Insulin Analog Expression Vectors

In order to prepare an insulin analog in which A-chain or B-chain amino acid of insulin is changed, using a native insulin expression vector as a template, forward and reverse oligonucleotides were synthesized (Table 2) and then PCR was performed, thereby amplifying the respective analog gene.

The changed sequences of amino acid of the A-chain or B-chain and the analog name thereof are shown in Table 1. That is, Analog 1 is a form in which glycine at position 1 of the A-chain was substituted with alanine, and Analog 4 is a form in which glycine at position 8 of the B-chain is substituted with alanine.

TABLE 1

| Analog | Modifed sequence |
| --- | --- |
| Analog 1 | $A^1G \rightarrow A$ |
| Analog 2 | $A^2I \rightarrow A$ |
| Analog 3 | $A^{19}Y \rightarrow A$ |
| Analog 4 | $B^8G \rightarrow A$ |
| Analog 5 | $B^{23}G \rightarrow A$ |
| Analog 6 | $B^{24}F \rightarrow A$ |
| Analog 7 | $B^{25}F \rightarrow A$ |
| Analog 8 | $A^{14}Y \rightarrow E$ |
| Analog 9 | $A^{14}Y \rightarrow N$ |

Primers for the amplification of insulin analog are shown in Table 2.

TABLE 2

| Analog | Sequence | SEQ ID NO |
|---|---|---|
| Analog 1 | 5' GGGTCCCTGCAGAAGCGTGCGATTGTGGAACAATGCTGT 3' | SEQ ID NO 1 |
|  | 5' ACAGCATTGTTCCACAATCGCACGCTTCTGCAGGGACCC 3' | SEQ ID NO 2 |
| Analog 2 | 5' TCCCTGCAGAAGCGTGGCGCGGTGGAACAATGCTGTACC 3' | SEQ ID NO 3 |
|  | 5' GGTACAGCATTGTTCCACCGCGCCACGCTTCTGCAGGGA 3' | SEQ ID NO 4 |
| Analog 3 | 5' CTCTACCAGCTGGAAAACGCGTGTAACTGAGGATCC 3' | SEQ ID NO 5 |
|  | 5' GGATCCTCAGTTACACGCGTTTTCCAGCTGGTAGAG 3' | SEQ ID NO 6 |
| Analog 4 | 5' GTTAACCAACACTTGTGTGCGTCACACCTGGTGGAAGCT 3' | SEQ ID NO 7 |
|  | 5' AGCTTCCACCAGGTGTGACGCACACAAGTGTTGGTTAAC 3' | SEQ ID NO 8 |
| Analog 5 | 5' CTAGTGTGCGGGGAACGAGCGTTCTTCTACACACCCAAG 3' | SEQ ID NO 9 |
|  | 5' CTTGGGTGTGTAGAAGAACGCTCGTTCCCCGCACACTAG 3' | SEQ ID NO 10 |
| Analog 6 | 5' GTGTGCGGGGAACGAGGCGCGTTCTACACACCCAAGACC 3' | SEQ ID NO 11 |
|  | 5' GGTCTTGGGTGTGTAGAACGCGCCTCGTTCCCCGCACAC 3' | SEQ ID NO 12 |
| Analog 7 | 5' TGCGGGGAACGAGGCTTCGCGTACACACCCAAGACCCGC 3' | SEQ ID NO 13 |
|  | 5' GCGGGTCTTGGGTGTGTACGCGAAGCCTCGTTCCCCGCA 3' | SEQ ID NO 14 |
| Analog 8 | 5'-CCAGCATCTGCTCCCCTCGAACAGCTGGAGAACTACTG-3' | SEQ ID NO 15 |
|  | 5'-Cagtagttctccagctgttcgagggagcagatgctgg-3' | SEQ ID NO 16 |
| Analog 9 | 5'-CAGCATCTGCTCCCTCAACCAGCTGGAGAACTAC-3' | SEQ ID NO 17 |
|  | 5'-Gtagttctccagctggttgagggagcagatgctg-3' | SEQ ID NO 18 |

PCR condition for the amplification of the insulin analogue was at 95° C. for 30 seconds, at 55° C. for 30 seconds and 68° C. for minutes and this procedure was repeated 18 times. The insulin analog fragment obtained under these conditions was inserted into pET22b expression vector to express in the form of inclusion bodies within the cell. The expression vector thus obtained was named pET22b-insulin analogs 1-9. The expression vector includes a nucleic acid encoding the amino acid sequence of the insulin analogs 1 to 9 under the control of the T7 promoter, and the expression vector was expressed in the form of inclusion bodies in the host.

The DNA sequences and protein sequences of each of the insulin analogs 1 to 9 are shown in Table 3 below.

TABLE 3

| Analog | | Sequence | SEQ ID NO |
|---|---|---|---|
| Analog 1 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GGC CTG GAG GGG TCC CTG CAG AAG CGT GCG ATT GTG GAA CAA TGC TGT ACC AGC ATC TGC TCC CTC TAC CAG CTG GAG AAC TAC TGC AAC | 19 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Ala Ile Val Glu Gln Cys Cys Thr Ser Ile Cys Ser Leu Tyr Gln Leu Glu Asn Tyr Cys Asn | 20 |
| Analog 2 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC GCG GTG GAA CAA TGC TGT ACC AGC ATC TGC TCC CTC TAC CAG CTG GAG AAC TAC TGC AAC | 21 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Pro Gly Ala Gly Ser Leu Gln Pro Leu Ala Leu Glu Gly Ser Leu Gln Lys Arg Gly Ala Val Glu Gln Cys Cys Thr Ser Ile Cys Ser Leu Tyr Gln Leu Glu Asn Tyr Cys Asn | 22 |

TABLE 3-continued

| Analog | | Sequence | SEQ ID NO |
|---|---|---|---|
| Analog 3 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC TAC CAG CTG GAG AAC GCG TGC AAC | 23 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Ala Cys Asn | 24 |
| Analog 4 | DNA | TTC GTT AAC CAA CAC TTG TGT GCG TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC TAC CAG CTG GAG AAC TAC TGC AAC | 25 |
| | Protein | Phe Val Asn Gln His Leu Cys Ala Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn | 26 |
| Analog 5 | DNA | TTC GTT AAC CAA CAC TTG TGT GGC TCA CAC CTG GTG GAA GCT CTC TAC CTA GTG TGC GGG GAA CGA GCG TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC TAC CAG CTG GAG AAC TAC TGC AAC | 27 |
| | Protein | Phe Val Asn Gln His Leu Cys Gly Ser His Leu Val Glu Ala Leu Tyr Leu Val Cys Gly Glu Arg Ala Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn | 28 |
| Analog 6 | DNA | TTC GTT AAC CAA CAC TTG TGT GGC TCA CAC CTG GTG GAA GCT CTC TAC CTA GTG TGC GGG GAA CGA GGC GCG TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC TAC CAG CTG GAG AAC TAC TGC AAC | 29 |
| | Protein | Phe Val Asn Gln His Leu Cys Gly Ser His Leu Val Glu Ala Leu Tyr Leu Val Cys Gly Glu Arg Gly Ala Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn | 30 |
| Analog 7 | DNA | TTC GTT AAC CAA CAC TTG TGT GGC TCA CAC CTG GTG GAA GCT CTC TAC CTA GTG TGC GGG GAA CGA GGC TTC GCG TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC TAC CAG CTG GAG AAC TAC TGC AAC | 31 |

TABLE 3-continued

| Analog | | Sequence | SEQ ID NO |
|---|---|---|---|
| | Protein | Phe Val Asn Gln His Leu Cys Gly Ser His Leu Val Glu Ala<br>Leu Tyr Leu Val Cys Gly Glu Arg Gly Phe Ala Tyr Thr Pro<br>Lys Thr Arg Arg Glu Ala Glu Asp Leu Gln Val Gly Gln Val<br>Glu Leu Gly Gly Gly Pro Gly Ala Gly Ser Leu Gln Pro Leu<br>Ala Leu Glu Gly Ser Leu Gln Lys Arg Gly Ile Val Glu Gln<br>Cys Cys Thr Ser Ile Cys Ser Leu Tyr Gln Leu Glu Asn Tyr<br>Cys Asn | 32 |
| Analog 8 | DNA | TTC GTT AAC CAA CAC TTG TGT GGC TCA CAC CTG GTG GAA GCT<br>CTC TAC CTA GTG TGC GGG GAA CGA GGC TTC TTC TAC ACA CCC<br>AAG ACC CGC CGG GAG GCA GAG GAC CTG CAG GTG GGG CAG GTG<br>GAG CTG GGC GGG GGC CCT GGT GCA GGC AGC CTG CAG CCC TTG<br>GCC CTG GAG GGG TCC CTG CAG AAG CGT GGC ATT GTG GAA CAA<br>TGC TGT ACC AGC ATC TGC TCC CTC GAA CAG CTG GAG AAC TAC<br>TGC AAC TGA | 33 |
| | Protein | Phe Val Asn Gln His Leu Cys Gly Ser His Leu Val Glu Ala<br>Leu Tyr Leu Val Cys Gly Glu Arg Gly Phe Phe Tyr Thr Pro<br>Lys Thr Arg Arg Glu Ala Glu Asp Leu Gln Val Gly Gln Val<br>Glu Leu Gly Gly Gly Pro Gly Ala Gly Ser Leu Gln Pro Leu<br>Ala Leu Glu Gly Ser Leu Gln Lys Arg Gly Ile Val Glu Gln<br>Cys Cys Thr Ser Ile Cys Ser Leu Glu Gln Leu Glu Asn Tyr<br>Cys Asn | 34 |
| Analog 9 | DNA | TTC GTT AAC CAA CAC TTG TGT GGC TCA CAC CTG GTG GAA GCT<br>CTC TAC CTA GTG TGC GGG GAA CGA GGC TTC TTC TAC ACA CCC<br>AAG ACC CGC CGG GAG GCA GAG GAC CTG CAG GTG GGG CAG GTG<br>GAG CTG GGC GGG GGC CCT GGT GCA GGC AGC CTG CAG CCC TTG<br>GCC CTG GAG GGG TCC CTG CAG AAG CGT GGC ATT GTG GAA CAA<br>TGC TGT ACC AGC ATC TGC TCC CTC AAC CAG CTG GAG AAC TAC<br>TGC AAC TGA | 35 |
| | Protein | Phe Val Asn Gln His Leu Cys Gly Ser His Leu Val Glu Ala<br>Leu Tyr Leu Val Cys Gly Glu Arg Gly Phe Phe Tyr Thr Pro<br>Lys Thr Arg Arg Glu Ala Glu Asp Leu Gln Val Gly Gln Val<br>Glu Leu Gly Gly Gly Pro Gly Ala Gly Ser Leu Gln Pro Leu<br>Ala Leu Glu Gly Ser Leu Gln Lys Arg Gly Ile Val Glu Gln<br>Cys Cys Thr Ser Ile Cys Ser Leu Asn Gln Leu Glu Asn Tyr<br>Cys Asn | 36 |

Example 2: Expression of Recombinant Insulin Analog Fusion Polypeptide

The expression of recombinant insulin analog was performed under T7 promoter control. *E. coli* BL21-DE3 (*E coli* B F-dcm ompT hsdS (rB-mB-) gal DE3.); Nova Zen) was transformed with each recombinant insulin analog expression vector. The transformation was performed following the method recommended by the Novagene. The individual single colonies in which each recombinant expression vector was transformed was taken, inoculated in 2×Luria broth (LB) medium containing ampicillin (50/ml), and incubated at 37° C. for 15 hours. The recombinant strain culture and the 2×LB medium containing 30% glycerol were mixed in a ratio of 1:1 (v/v). 1 ml per the culture was then dispensed into cryo-tubes and kept at −140° C. This was used as a cell stock for the production of a recombinant fusion protein.

For the expression of recombinant insulin analog, each cell stock 1 vial was dissolved, inoculated with 500 ml of 2×Luria broth and cultured with shaking at 37° C. for 14-16 hours. When the value of OD600 indicates 5.0 or greater, the culture was completed and used as a seed culture. The seed culture was inoculated in 17 L of fermentation medium using 50 L fermentor (MSJ-U2, BEMARUBISHI, Japan), and the initial bath fermentation was started. The culture conditions were a temperature of 37° C., an air volume of 20 L/min (1 vvm), and a stirring speed of 500 rpm and maintained at pH 6.70 using a 30% ammonia water. When nutrient in the culture medium was limited in the fermentation progress, the batch culture was performed by adding a feeding solution. The growth of strains was monitored by OD values and introduced into IPTG with a final concentration of 500 M at the OD values of 100 or more. The culture was further performed by about 23 to 25 hours after introduction. After completion of the culture, a recombinant strain were harvested via centrifugation and stored at −80° C. until use.

Example 3: Number and Refolding of Recombinant Insulin Analog

In order to change the recombinant insulin analogs expressed in Example 2 in a soluble form, the cells were crushed and refolded. 100 g (wet weight) of cell pellet was re-suspended in 1 L lysis buffer (50 mM Tris-HCl (pH 9.0), 1 mM EDTA (pH 8.0), 1 mM EDTA (pH 8.0), 0.2 M NaCl and 0.5% Triton X-100). The cells were crushed using a microfluidizer processor M-110EH (AC Technology Corp. Model M1475C) at a pressure of 15,000 psi. The crushed cell lysate was centrifuged at 7,000 rpm at 4° C. for 20 minutes to discard the supernatant and re-suspended in 3 L wash buffer (0.5% Triton X-100 and 50 mM Tris-HCl (pH 8.0), 0.2 M NaCl, 1 mM EDTA). The pellet was centrifuged at 7,000 rpm at 4° C. for 20 minutes and re-suspended in distilled water and then centrifuged in the same way. The pellet was taken, re-suspended in 400 ml of buffer solution (1 M glycine, 3.78 g cysteine-HCl, pH 10.6) and then stirred at room temperature for 1 hour. To collect the re-suspended recombinant insulin analog, 400 ml of 8M urea was added and then stirred at 40° C. for 1 hour. In order to refold the solubilized recombinant insulin analog, it was centrifuged at 7,000 rpm at 4° C. for 30 minutes. Then the supernatant was taken to which 2 L of distilled water was added at a flow rate of 1000 ml/hr using a peristaltic pump and stirred at 4° C. for 16 hours.

Example 4: Cation Binding Chromatographic Purification

The refolded sample was combined bound to Source S (GE healthcare, Inc.) column equilibrated with 20 mM of sodium citrate contained in the site is equilibrated with 45% ethanol (pH 2.0) buffer containing 4% ethanol. The insulin analog protein was then eluted with 10 column volume of linear gradient using 20 mM sodium citrate (pH 2.0) buffer containing 45% ethanol and 0.5 M of potassium chloride so that the concentration is 0% to 100%.

Example 5: Treatment of Trypsin and Carboxypeptidase B

The salt was removed from a sample eluted with desalting column, and replaced with a buffer solution (10 mM Tris-HCl, pH 8.0). Trypsin corresponding to a 1000 mole ratio of the resulting sample protein amount and carboxy peptidase B corresponding to a 2000 mole ratio were added and then stirred at 16° C. for 16 hours. In order to complete the reaction, pH was lowered to 3.5 using 1 M sodium citrate (pH 2.0).

Example 6: Cationic Coupled Chromatographic Purification

The Reaction-Completed Sample was Again Combined with Source S (GE healthcare, Inc.) column equilibrated with 20 mM sodium citrate (pH 2.0) buffer containing 45% ethanol. The insulin analog protein was then eluted with 10 column volume of linear gradient using 20 mM sodium citrate (pH 2.0) buffer containing 45% ethanol and 0.5 M of potassium chloride so that the concentration is 0% to 100%.

Example 7: Anion Binding Chromatographic Purification

The salt was removed from a sample eluted with a desalting column, and replaced with a buffer solution (10 mM Tris-HCl, pH 7.5). In order to separate a pure insulin analog from the sample obtained in Example 6, the sample was combined with an anion exchange column (Source Q: GE healthcare, Inc.) equilibrated with 10 mM tris (pH 7.5) buffer solution. The insulin analog protein was then eluted with 10 column volume of linear gradient using 10 mM tris (pH 7.5) buffer solution containing 0.5M sodium chloride so that the concentration is 0% to 100%.

The purity of the purified insulin analog were analyzed using protein electrophoresis (SDS-PAGE) and high-pressure chromatography (HPLC), and the amino acid changes were confirmed through a peptide mapping and a molecular weight analysis of each peak.

As a result, it was confirmed that the amino acid sequence was changed according to a desired purpose of respective insulin analog.

Example 8: Preparation of Long-Acting Insulin Conjugate

In this example, the long-acting insulin conjugate of the sequence analog (Glu at position 14 of the A-chain) of a native insulin analogue, a typical insulin analogue, was prepared.

In order to PeGylate 3.4K ALD2 PEG (NOF, Japan) at the N-terminal of the insulin analog beta chain, the insulin analog and PEG were allowed to react with each other at a molar ratio of 1:4 at an insulin analog concentration of 5 mg/ml at 4~8° C. for about 2 hours. At this time, the reaction was carried out in 50 mM sodium citrate pH 6.0, 40~60% isopropanol, and the reaction was carried out by adding 3.0~20.0 mM concentration of a reducing agent of sodium cyanoborohydride. The reaction solution was purified using a SP-HP (GE Healthcare, USA) column containing ethanol in sodium citrate (pH 3.0).

In order to prepare an insulin analog-immunoglobulin Fc fragment conjugate, the purified mono-PEGylated insulin analog and the immunoglobulin Fc fragment were allowed to react with each other at a molar ratio of 1:1 to 1:2 at a total protein concentration of 20 mg/ml at 25° C. for about 12~16 hours. At this time, the reaction buffer condition was 100 mM HEPES, pH 8.2 to which 20 mM of sodium cyanoborohydride hydride was added as a reducing agent to prepare a insulin analog conjugate PEG-modified at the N-terminal of the Fc fragment.

Upon completion of the reaction, the reaction solution was applied to Q HP (GE Healthcare, USA) column and the insulin analog-immunoglobulin Fc fragment conjugate was first purified using Tris-HCl (pH 7.5) buffer with NaCl concentration gradient.

Subsequently, the insulin analog-immunoglobulin Fc fragment conjugate was obtained using Source 15ISO (GE Healthcare, USA) as a second column. At this time, the insulin analog-immunoglobulin Fc fragment conjugate was eluted using a concentration gradient of ammonium sulfate containing Tris-HCl (pH 7.5).

Example 9: Synthesis of Oxyntomodulin Derivatives

In the example, oxyntomodulin derivatives having the following amino acid sequences were synthesized (Table 4).

TABLE 4

| SEQ ID NO. | Amino acid sequence | Note |
| --- | --- | --- |
| SEQ ID NO. 39 | HSQGTFTSDYSKYLDSRRAQDFVQWLMNTKRNRNNIA | |
| SEQ ID NO. 40 | HAibQGTFTSDYSKYLD<u>E</u>KRA<u>K</u>EFVQWLMNTC | Ring formation |

TABLE 4-continued

| SEQ ID NO. | Amino acid sequence | Note |
|---|---|---|
| SEQ ID NO. 41 | CA-SQGTFTSDYSKYLDEEAVRLFIEWLMNTKRNRNNIA | |
| SEQ ID NO. 42 | CA-SQGTFTSDYSKYLDERRAQDFVAWLKNTGPSSGAPPPS | |
| SEQ ID NO. 43 | CA-GQGTFTSDYSRYLEEEAVRLFIEWLKNGGPSSGAPPPS | |
| SEQ ID NO. 44 | CA-GQGTFTSDYSRQMEEEAVRLFIEWLKNGGPSSGAPPPS | |
| SEQ ID NO. 45 | CA-GEGTFTSDLSRQMEEEAVRLFIEWAAHSQGTFTSDYSKYLD | |
| SEQ ID NO. 46 | CA-SQGTFTSDYSRYLDEEAVRLFIEWLMNTK | |
| SEQ ID NO. 47 | CA-SQGTFTSDLSRQLEEEAVRLFIEWLMNK | |
| SEQ ID NO. 48 | CA-GQGTFTSDYSRYLDEEAVXLFIEWLMNTKRNRNNIA | |
| SEQ ID NO. 49 | CA-SQGTFTSDYSRQMEEEAVRLFIEWLMNGGPSSGAPPPSK | |
| SEQ ID NO. 50 | CA-GEGTFTSDLSRQMEEEAVRLFIEWAAHSQGTFTSDYSRYLDK | |
| SEQ ID NO. 51 | CA-SQGTFTSDYSRYLDGGGHGEGTFTSDLSKQMEEEAVK | |
| SEQ ID NO. 52 | CA-SQGTFTSDYSRYLDXEAVXLFIEWLMNTK | |
| SEQ ID NO. 53 | CA-GQGTFTSDYSRYLDEEAVXLFIXWLMNTKRNRNNIA | |
| SEQ ID NO. 54 | CA-GQGTFTSDYSRYLDEEAVRLFIXWLMNTKRNRNNIA | |
| SEQ ID NO. 55 | CA-SQGTFTSDLSRQLEGGGHSQGTFTSDLSRQLEK | |
| SEQ ID NO. 56 | CA-SQGTFTSDYSRYLDEEAVRLFIEWIRNTKRNRNNIA | |
| SEQ ID NO. 57 | CA-SQGTFTSDYSRYLDEEAVRLFIEWIRNGGPSSGAPPPSK | |
| SEQ ID NO. 58 | CA-SQGTFTSDYSRYLDEEAVKLFIEWIRNTKRNRNNIA | Ring Formation |
| SEQ ID NO. 59 | CA-SQGTFTSDYSRYLDEEAVKLFIEWIRNGGPSSGAPPPSK | Ring Formation |
| SEQ ID NO. 60 | CA-SQGTFTSDYSRQLEEEAVRLFIEWVRNTKRNRNNIA | |
| SEQ ID NO. 61 | DA-SQGTFTSDYSKYLDEKRAKEFVQWLMNTK | Ring Formation |
| SEQ ID NO. 62 | HAibQGTFTSDYSKYLDEKRAKEFVCWLMNT | |
| SEQ ID NO. 63 | HAibQGTFTSDYSKYLDEKRAKEFVQWLMNTC | |
| SEQ ID NO. 64 | HAibQGTFTSDYSKYLDEKRAKEFVQWLMNTC | Ring Formation |
| SEQ ID NO. 65 | HAibQGTFTSDYSKYLDEQAAKEFICWLMNT | Ring Formation |
| SEQ ID NO. 66 | HAibQGTFTSDYSKYLDEKRAKEFVQWLMNT | |
| SEQ ID NO. 67 | H(d)SQGTFTSDYSKYLDSRRAQDFVQWLMNTKRNRNNIA | |
| SEQ ID NO. 68 | CA-SQGTFTSDYSKYLDSRRAQDFVQWLMNTKRNRNNIA | |
| SEQ ID NO. 69 | CA-(d)SQGTFTSDYSKYLDSRRAQDFVQWLMNTKRNRNNIA | |
| SEQ ID NO. 70 | CA-AibQGTFTSDYSKYLDEKRAKEFVQWLMNTC | Ring Formation |
| SEQ ID NO. 71 | HAibQGTFTSDYAKYLDEKRAKEFVQWLMNTC | Ring Formation |
| SEQ ID NO. 72 | YAibQGTFTSDYSKYLDEKRAKEFVQWLMNTC | Ring Formation |

In Table 4, the amino acids in bold and underlined in each of SEQ ID NOS: 19, 20, 22, 25, 26, 27, 32, 33, and 34, taken together, form a ring, and the amino acids represented by X mean a non-native amino acid, alpha-methyl-glutamic acid. In addition, CA represents 4-imidazoacetyl, and DA represents desamino-histidyl.

Example 10: Production of Long-Acting GLP-1/Glucagon Dual Agonist Conjugate

In this example, a long-acting conjugate of a native oxyntomodulin variant, a typical GLP-1/glucagon dual agonist, was prepared.

First, in order to PEGylate MAL-10K-ALD PEG at cysteine residue at position 30 of the amino acid sequence of the GLP-1/glucagon dual agonist and (SEQ ID NO: 40: HAibQGTFTSDYSKYLDEKRAKEFVQWLMNTC, amino acids shown in bold means a ring formation, Aib is 2-methylalanine), the GLP-1/glucagon dual agonist and MAL-10K-ALD (NOF, Japan) PEG were allowed to react with each other at a molar ratio of 1:1 to 1:3 at a protein concentration of 3~5 mg/ml at room temperature for about 3 hours. At this time, the reaction was carried out in the environment wherein isopropanol was added to 50 mM Tris buffer (pH 8.0). Upon completion of the reaction, the reaction solution was applied to SP HP (GE, USA) column and the GLP-1/glucagon dual agonist mono-pegylated with cysteine was purified. Purification method was performed using a sodium citrate pH 3.0 buffer containing ethanol and a potassium chloride concentration gradient.

Next, the purified mono-pegylated GLP-1/glucagon dual agonist and immunoglobulin Fc were allowed to react with each other at a molar ratio of about 1:2 to 1:5 at a protein concentration of about 20 mg/ml at 4~8° C. for 12 to 16 hours. The reaction was carried in environment wherein 20 mM of SCB was added as a reducing agent to 100 mM if potassium phosphate buffer (pH 6.0). Upon completion of the reaction, as the reaction solution, SOURCE Q (GE, USA) was used to first purify the GLP-1/glucagon dual agonist-immunoglobulin Fc fragment conjugate. The purification was performed using 20 mM bistris buffer pH 6.8 and a concentration gradient of sodium chloride. Then, the GLP-1/glucagon dual agonist-immunoglobulin Fc fragment conjugate was finally purified using Source ISO purification column. The GLP-1/glucagon dual agonist-immunoglobulin Fc fragment conjugate was purified using 20 mM Tris buffer pH 7.5 containing 1 M of ammonium sulfate and a concentration gradient of 20 mM Tris buffer pH 7.5.

Example 11: Evaluation of the Effect by a Combined Administration of the GLP-1/Glucagon Dual Agonist-Immunoglobulin Fc Conjugate and an Insulin Analog-Immunoglobulin Fc Conjugate The present test was carried out to determine the progress of the blood glucose level and the body weight change upon combined administration of the long-acting GLP-1/glucagon dual agonist conjugate and the long-acting insulin analog conjugate prepared in Examples 9 and 10. 42 db/db rats (7-week-old) was acclimated for 2 weeks in a condition of free-taking diet and water and then 6 rats per group were divided into 7 rats in total. The groups according to the administration materials are 7 groups in total which include vehicle, GLP-1/glucagon dual agonist-immunoglobulin Fc conjugate alone-treated group (1.4 nmol/kg), insulin analog-immunoglobulin Fc conjugate alone-treated group (8.8 and 17.6 nmol/kg), long-acting GLP-1/glucagon dual agonist-immunoglobulin Fc conjugate-combined treated group (2.2, 4.4, and 8.8 nmol/kg). All test materials were administered subcutaneously twice daily. Except for the day which performs administration, the blood glucose levels were measured with glucometer after fasting for 4 hours randomly twice a week. The blood glucose level of each group was compared by an AUC (area under the curve) graph showing the fasting glucose change for 4 weeks as compared with a vehicle-treated group (FIG. 1). The weight changes were compared after administration of drug for 4 weeks in each group as compared with pre-dose (FIG. 2)

As shown in FIG. 1, as compared with a single administration group of the GLP-1/glucagon dual agonist-immunoglobulin Fc conjugate (1.4 nmol/kg) or insulin analog-immunoglobulin Fc conjugate (8.8 nmol/kg), a synergy effect was shown in a combined administration group of the two materials in the same amount (GLP-1/glucagon dual agonist-immunoglobulin Fc conjugate (1.4 nmol/kg) or insulin analog-immunoglobulin Fc conjugate (8.8 nmol/kg)). Also, the combined administration group exhibited the effects of blood glucose level reduction similar to insulin analog-immunoglobulin Fc conjugate (17.6 nmol/kg) administered in a higher dose.

In the body weight change (FIG. 2), the insulin analog-immunoglobulin Fc conjugate exhibited increased body weight through repeated administration for 4 weeks, whereas a combined administration group and a single administration group of the long-acting GLP-1/glucagon dual agonist-immunoglobulin Fc conjugate exhibited reduced body weight.

Further, comparing a single-treated group of insulin analog-immunoglobulin Fc conjugate in which the same amount of insulin analog-immunoglobulin was administered with a combined treated group of GLP-1/glucagon dual agonist-immunoglobulin Fc conjugate/insulin, the weight gain due to the administration of insulin could be prevented by administrating GLP-1/glucagon dual agonist-immunoglobulin Fc conjugate together. In addition, even if a single-treated group of insulin analog-immunoglobulin Fc conjugate (17.6 nmol/kg) was compared with a combined treated group (GLP-1/glucagon dual agonist-immunoglobulin Fc conjugate (1.4 nmol/kg), insulin analog-immunoglobulin Fc conjugate (8.8 nmol/kg)), it could be seen that there was an effect of body weight reduction.

From these results, it was seen that the composition including both a long-acting insulin conjugate and a long-acting GLP-1/glucagon dual agonist conjugate has excellent ability to control blood glucose levels and has no side-effects of weight gain due to the administration of insulin exhibited superior therapeutic effect than the group in which conventional insulin and dual agonist drug were administered, respectively.

From the above description, a person skilled in the art will appreciate that the invention may be embodied in other specific forms without changing the technical spirit or essential characteristics. In this regard, the embodiments described above should be understood to be illustrative rather than restrictive in every respect. The scope of the invention should be construed that the meaning and scope of the appended claims rather than the detailed description and all changes or variations derived from the equivalent concepts fall within the scope of the present invention.

The invention claimed is:

1. A method for treating diabetes mellitus, comprising administering a pharmaceutical composition to a subject at high risk of or having the diabetes mellitus, wherein the composition comprises a long-acting insulin conjugate and a long-acting glucagon-like peptide (GLP-1)/glucagon dual agonist conjugate,
   wherein the long-acting insulin conjugate is a conjugate in which insulin is linked to an immunoglobulin Fc region via a non-peptidyl polymer; and
   wherein the long-acting GLP-1/glucagon dual agonist conjugate is a conjugate in which a GLP-1/glucagon dual agonist is linked to an immunoglobulin Fc region via a non-peptidyl polymer.

2. The method according to claim 1, wherein the insulin is native insulin, rapid-acting insulin, basal insulin, an insulin analog which is an insulin variant prepared by any one of substitution, addition, deletion, modification, or a combination thereof of the amino acid sequence of the native insulin, or a fragment thereof, and
   wherein the GLP-1/glucagon dual agonist simultaneously activates GLP-1 receptor and glucagon receptors.

3. The method according to claim 1, wherein the long-acting GLP-1/glucagon dual agonist has the amino acid sequence of SEQ ID NO: 40 and the amino acids at positions 16 and 20 form a ring.

4. The method according to claim 1, wherein
   (i) the non-peptidyl polymer is selected from the group consisting of polyethylene glycol, polypropylene glycol, an ethylene glycol-propylene glycol copolymer, polyoxyethylated polyol, polyvinyl alcohol, a polysaccharide, dextran, polyvinyl ethyl ether, a biodegradable polymer, a lipid polymer, chitin, hyaluronic acid, and a combination thereof; and/or
   (ii) the immunoglobulin Fc region is aglycosylated.

5. The method according to claim 4, wherein the immunoglobulin Fc region comprises one to four region(s) selected from the group consisting of CH1, CH2, CH3 and CH4 domains.

6. The method according to claim 5, wherein the immunoglobulin Fc region further comprises a hinge region.

7. The method according to claim 6, wherein the immunoglobulin Fc region is an Fc region derived from IgG, IgA, IgD, IgE, or IgM.

8. The method according to claim 7, wherein each domain of the immunoglobulin Fc region is a hybrid of domains having a different origin selected from the group consisting of IgG, IgA, IgD, IgE, and IgM.

9. The method according to claim 8, wherein the immunoglobulin Fc region is a dimer or a multimer consisting of single-chain immunoglobulins consisting of domains having the same origin.

10. The method according to claim 1, wherein the pharmaceutical composition further comprises a pharmaceutically acceptable carrier.

11. The method according to claim 1, wherein the insulin is an insulin analog comprising a substitution of the $14^{th}$ amino acid in the insulin A-chain with a glutamic acid, and
    wherein the long-acting GLP-1/glucagon dual agonist is represented by SEQ ID NO: 40.

12. The method according to claim 11, wherein the $16^{th}$ and $20^{th}$ amino acids of the GLP-1/glucagon dual agonist of SEQ ID NO: 40 form a ring.

13. The method according to claim 1, wherein the non-peptidyl polymer linker is PEG.

14. The method according to claim 1, wherein the administering step is performed by a combined administration of the long-acting insulin conjugate and the long-acting GLP-1/glucagon dual agonist conjugate.

15. The method according to claim 14, wherein the combined administration is performed by simultaneously, sequentially, or reversely administrating the long-acting insulin conjugate and the long-acting GLP-1/glucagon dual agonist conjugate.

* * * * *